(12) United States Patent
Pages

(10) Patent No.: US 9,567,627 B2
(45) Date of Patent: Feb. 14, 2017

(54) METHOD FOR PREDICTING THE RESPONSE TO TREATMENT WITH AN HER2-BLOCKING AGENT

(75) Inventor: Gilles Pages, Monaco (MC)

(73) Assignees: UNIVERSITE DE NICE SOPHIA ANTIPOLIS, Nice (FR); CENTRE NATIONAL DE LA RECHERCHE SCIENTIFIQUE (CNRS), Paris (FR)

( * ) Notice: Subject to any disclaimer, the term of this patent is extended or adjusted under 35 U.S.C. 154(b) by 0 days.

(21) Appl. No.: 14/125,155

(22) PCT Filed: Jun. 7, 2012

(86) PCT No.: PCT/EP2012/060807
§ 371 (c)(1),
(2), (4) Date: Dec. 10, 2013

(87) PCT Pub. No.: WO2012/168370
PCT Pub. Date: Dec. 13, 2012

(65) Prior Publication Data
US 2014/0377252 A1  Dec. 25, 2014

(30) Foreign Application Priority Data
Jun. 10, 2011 (FR) .................... 11 55128

(51) Int. Cl.
| | | |
|---|---|---|
| C12Q 1/68 | (2006.01) | |
| A61K 39/395 | (2006.01) | |
| G01N 33/574 | (2006.01) | |
| A61K 45/06 | (2006.01) | |

(52) U.S. Cl.
CPC ......... *C12Q 1/6827* (2013.01); *A61K 39/3955* (2013.01); *A61K 45/06* (2013.01); *C12Q 1/6886* (2013.01); *G01N 33/57415* (2013.01); *G01N 33/57484* (2013.01); *G01N 33/57492* (2013.01); *C12Q 2600/106* (2013.01); *C12Q 2600/156* (2013.01); *G01N 2500/04* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 6,355,623 B2* | 3/2002 | Seidman et al. .................. 514/45 | |
| 2008/0102069 A1* | 5/2008 | Friess et al. ................ 424/133.1 | |
| 2010/0055705 A1 | 3/2010 | Wilson et al. | |
| 2011/0038862 A1* | 2/2011 | Sotiriou ............... | C12Q 1/6886 424/133.1 |

FOREIGN PATENT DOCUMENTS

| | | |
|---|---|---|
| WO | WO 01/79226 A2 | 10/2001 |
| WO | WO 2006/010938 A1 | 2/2006 |
| WO | WO 2006/098978 A1 | 9/2006 |
| WO | WO 2011/071232 A1 | 6/2011 |

OTHER PUBLICATIONS

Taber's Cyclopedic Medical Dictionary (1985, F.A. Davis Company, Philadelphia, p. 274).*
Busken, C et al. (Digestive Disease Week Abstracts and Itinerary Planner, 2003, abstract No. 850).*
Kaiser (Science, 2006, 313: 1370).*
Krontiris and Capizzi (Internal Medicine, 4th Edition, Editor-in-chief Jay Stein, Elsevier Science, 1994 Chapters 71-72, pp. 699-729).*
Carter, S. K. et al. (Chemotherapy of Cancer; Second edition; John Wiley & Sons: New York, 1981.*
Pritzker (Clinical Chemistry, 2002, 48:1147-1150).*
Adlard et al. (The Lancet Oncology, Feb. 2002, 3:75-82).*
Guedj et al. (J. Invest. Dermatology Sep. 2009 129: Suppl. 2 pp. S89, Abstract No. 529 [Oral 095]).*
Al-Souhibani et al., "The RNA Binding Zinc-Finger Protein Tristetraprolin Regulates AU-Rich mRNAs Involved in Breast Cancer-Related Processes," Oncogene, vol. 29, No. 29, 2010 (Published online: May 24, 2010), pp. 4205-4215, XP055018343.
Brennan et al., "The mRNA-destabilizing protein tristetraprolin is suppressed in many cancers, altering tumorigenic phenotypes and patient prognosis," Cancer Research, vol. 69, No. 12, 2009 (Published online Jun. 2, 2009), pp. 5168-5176, XP055018341.
Carrick et al., "Genetic variations in ZFP36 and their possible relationship to autoimmune diseases," Journal of Autoimmunity, vol. 26, 2006, pp. 182-196, XP024910079.
Griseri et al., "A synonymous polymorphism of the Tristetraprolin (TTP) gene, an AU-rich mRNA-binding protein, affects translation efficiency and response to Herceptin treatment in breast cancer patients," Human Molecular Genetics, vol. 20, No. 23, 2011, pp. 4556-4568, XP055018206.
International Search Report and Written Opinion of the International Searching Authority dated Aug. 17, 2012, for International Application No. PCT/EP2012/060807 (Forms PCT/ISA/210 and PCT/ISA/237).
Lee et al., "Tristetraprolin regulates expression of VEGF and tumorigenesis in human colon cancer," International Journal of Cancer, vol. 126, 2010, pp. 1817-1827, XP055018146.
Suswam et al., "Tristetraprolin down-regulates interleukin-8 and vascular endothelial growth factor in malignant glioma cells," Cancer Research, 2008 (Published online: Feb. 1, 2008), vol. 68, No. 3, pp. 674-682, XP055018342.
Van Tubergen et al., "Tristetraprolin regulates interleukin-6, which is correlated with tumor progression in patients with head and neck squamous cell carcinoma," Cancer, vol. 117, No. 2, Jun. 15, 2011, pp. 2677-2689, XP055018131.

* cited by examiner

*Primary Examiner* — Peter J Reddig
(74) *Attorney, Agent, or Firm* — Birch, Stewart, Kolasch & Birch, LLP

(57) ABSTRACT

The invention relates in particular to an in vitro or ex vivo method for predicting the response of a patient to treatment with at least one HER2-blocking agent, said method including the steps of: i) identifying the nucleotide at the rs3746083 polymorphic site, for at least one allele, in particular the two alleles of the gene coding the tristetraprolin protein, in a biological sample from said patient; and/or ii) determining the concentration of the tristetraprolin protein in a biological sample from said patient, wherein said patient is suffering from HER2-positive cancer.

3 Claims, 11 Drawing Sheets

ΔG=-46.80kcal/mol      ΔG=-49 kcal/mol

```
SEQUENCE LISTING

<160> NUMBER OF SEQ ID NOS: 10

<210> SEQ ID NO 1
<211> LENGTH: 1255
<212> TYPE: PRT
<213> ORGANISM: homo sapiens

<400> SEQUENCE: 1

Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
    50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys
```

-continued

```
            210                 215                 220
Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
                260                 265                 270

Thr Tyr Asn Thr Asp Thr Phe Glu Ser Met Pro Asn Pro Glu Gly Arg
                275                 280                 285

Tyr Thr Phe Gly Ala Ser Cys Val Thr Ala Cys Pro Tyr Asn Tyr Leu
                290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
                340                 345                 350

Val Arg Ala Val Thr Ser Ala Asn Ile Gln Glu Phe Ala Gly Cys Lys
                355                 360                 365

Lys Ile Phe Gly Ser Leu Ala Phe Leu Pro Glu Ser Phe Asp Gly Asp
                370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
                405                 410                 415

Asp Ser Leu Pro Asp Leu Ser Val Phe Gln Asn Leu Gln Val Ile Arg
                420                 425                 430

Gly Arg Ile Leu His Asn Gly Ala Tyr Ser Leu Thr Leu Gln Gly Leu
                435                 440                 445

Gly Ile Ser Trp Leu Gly Leu Arg Ser Leu Arg Glu Leu Gly Ser Gly
                450                 455                 460

Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
                485                 490                 495

Ala Asn Arg Pro Glu Asp Glu Cys Val Gly Glu Gly Leu Ala Cys His
                500                 505                 510

Gln Leu Cys Ala Arg Gly His Cys Trp Gly Pro Gly Pro Thr Gln Cys
                515                 520                 525

Val Asn Cys Ser Gln Phe Leu Arg Gly Gln Glu Cys Val Glu Glu Cys
                530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
                565                 570                 575

Phe Gly Pro Glu Ala Asp Gln Cys Val Ala Cys Ala His Tyr Lys Asp
                580                 585                 590

Pro Pro Phe Cys Val Ala Arg Cys Pro Ser Gly Val Lys Pro Asp Leu
                595                 600                 605

Ser Tyr Met Pro Ile Trp Lys Phe Pro Asp Glu Glu Gly Ala Cys Gln
                610                 615                 620

Pro Cys Pro Ile Asn Cys Thr His Ser Cys Val Asp Leu Asp Asp Lys
625                 630                 635                 640
```

```
Gly Cys Pro Ala Glu Gln Arg Ala Ser Pro Leu Thr Ser Ile Ile Ser
            645                 650                 655

Ala Val Val Gly Ile Leu Leu Val Val Leu Gly Val Val Phe Gly
            660                 665                 670

Ile Leu Ile Lys Arg Arg Gln Gln Lys Ile Arg Lys Tyr Thr Met Arg
            675                 680                 685

Arg Leu Leu Gln Glu Thr Glu Leu Val Glu Pro Leu Thr Pro Ser Gly
            690                 695                 700

Ala Met Pro Asn Gln Ala Gln Met Arg Ile Leu Lys Glu Thr Glu Leu
705                 710                 715                 720

Arg Lys Val Lys Val Leu Gly Ser Gly Ala Phe Gly Thr Val Tyr Lys
            725                 730                 735

Gly Ile Trp Ile Pro Asp Gly Glu Asn Val Lys Ile Pro Val Ala Ile
            740                 745                 750

Lys Val Leu Arg Glu Asn Thr Ser Pro Lys Ala Asn Lys Glu Ile Leu
            755                 760                 765

Asp Glu Ala Tyr Val Met Ala Gly Val Gly Ser Pro Tyr Val Ser Arg
            770                 775                 780

Leu Leu Gly Ile Cys Leu Thr Ser Thr Val Gln Leu Val Thr Gln Leu
785                 790                 795                 800

Met Pro Tyr Gly Cys Leu Leu Asp His Val Arg Glu Asn Arg Gly Arg
            805                 810                 815

Leu Gly Ser Gln Asp Leu Leu Asn Trp Cys Met Gln Ile Ala Lys Gly
            820                 825                 830

Met Ser Tyr Leu Glu Asp Val Arg Leu Val His Arg Asp Leu Ala Ala
            835                 840                 845

Arg Asn Val Leu Val Lys Ser Pro Asn His Val Lys Ile Thr Asp Phe
850                 855                 860

Gly Leu Ala Arg Leu Leu Asp Ile Asp Glu Thr Glu Tyr His Ala Asp
865                 870                 875                 880

Gly Gly Lys Val Pro Ile Lys Trp Met Ala Leu Glu Ser Ile Leu Arg
            885                 890                 895

Arg Arg Phe Thr His Gln Ser Asp Val Trp Ser Tyr Gly Val Thr Val
            900                 905                 910

Trp Glu Leu Met Thr Phe Gly Ala Lys Pro Tyr Asp Gly Ile Pro Ala
            915                 920                 925

Arg Glu Ile Pro Asp Leu Leu Glu Lys Gly Glu Arg Leu Pro Gln Pro
            930                 935                 940

Pro Ile Cys Thr Ile Asp Val Tyr Met Ile Met Val Lys Cys Trp Met
945                 950                 955                 960

Ile Asp Ser Glu Cys Arg Pro Arg Phe Arg Glu Leu Val Ser Glu Phe
            965                 970                 975

Ser Arg Met Ala Arg Asp Pro Gln Arg Phe Val Val Ile Gln Asn Glu
            980                 985                 990

Asp Leu Gly Pro Ala Ser Pro Leu Asp Ser Thr Phe Tyr Arg Ser Leu
            995                 1000                1005

Leu Glu Asp Asp Asp Met Gly Asp Leu Val Asp Ala Glu Glu Tyr
            1010                1015                1020

Leu Val Pro Gln Gln Gly Phe Phe Cys Pro Asp Pro Ala Pro Gly
            1025                1030                1035

Ala Gly Gly Met Val His His Arg His Arg Ser Ser Ser Thr Arg
            1040                1045                1050
```

```
Ser Gly Gly Gly Asp Leu Thr Leu Gly Leu Glu Pro Ser Glu Glu
    1055                1060                1065

Glu Ala Pro Arg Ser Pro Leu Ala Pro Ser Glu Gly Ala Gly Ser
    1070                1075                1080

Asp Val Phe Asp Gly Asp Leu Gly Met Gly Ala Ala Lys Gly Leu
    1085                1090                1095

Gln Ser Leu Pro Thr His Asp Pro Ser Pro Leu Gln Arg Tyr Ser
    1100                1105                1110

Glu Asp Pro Thr Val Pro Leu Pro Ser Glu Thr Asp Gly Tyr Val
    1115                1120                1125

Ala Pro Leu Thr Cys Ser Pro Gln Pro Glu Tyr Val Asn Gln Pro
    1130                1135                1140

Asp Val Arg Pro Gln Pro Pro Ser Pro Arg Glu Gly Pro Leu Pro
    1145                1150                1155

Ala Ala Arg Pro Ala Gly Ala Thr Leu Glu Arg Pro Lys Thr Leu
    1160                1165                1170

Ser Pro Gly Lys Asn Gly Val Val Lys Asp Val Phe Ala Phe Gly
    1175                1180                1185

Gly Ala Val Glu Asn Pro Glu Tyr Leu Thr Pro Gln Gly Gly Ala
    1190                1195                1200

Ala Pro Gln Pro His Pro Pro Ala Phe Ser Pro Ala Phe Asp
    1205                1210                1215

Asn Leu Tyr Tyr Trp Asp Gln Asp Pro Pro Glu Arg Gly Ala Pro
    1220                1225                1230

Pro Ser Thr Phe Lys Gly Thr Pro Thr Ala Glu Asn Pro Glu Tyr
    1235                1240                1245

Leu Gly Leu Asp Val Pro Val
    1250                1255

<210> SEQ ID NO 2
<211> LENGTH: 326
<212> TYPE: PRT
<213> ORGANISM: homo sapiens

<400> SEQUENCE: 2

Met Asp Leu Thr Ala Ile Tyr Glu Ser Leu Leu Ser Leu Ser Pro Asp
1               5                   10                  15

Val Pro Val Pro Ser Asp His Gly Gly Thr Glu Ser Ser Pro Gly Trp
            20                  25                  30

Gly Ser Ser Gly Pro Trp Ser Leu Ser Pro Ser Asp Ser Ser Pro Ser
        35                  40                  45

Gly Val Thr Ser Arg Leu Pro Gly Arg Ser Thr Ser Leu Val Glu Gly
    50                  55                  60

Arg Ser Cys Gly Trp Val Pro Pro Pro Gly Phe Ala Pro Leu Ala
65                  70                  75                  80

Pro Arg Leu Gly Pro Glu Leu Ser Pro Ser Pro Thr Ser Pro Thr Ala
                85                  90                  95

Thr Ser Thr Thr Pro Ser Arg Tyr Lys Thr Glu Leu Cys Arg Thr Phe
            100                 105                 110

Ser Glu Ser Gly Arg Cys Arg Tyr Gly Ala Lys Cys Gln Phe Ala His
        115                 120                 125

Gly Leu Gly Glu Leu Arg Gln Ala Asn Arg His Pro Lys Tyr Lys Thr
    130                 135                 140

Glu Leu Cys His Lys Phe Tyr Leu Gln Gly Arg Cys Pro Tyr Gly Ser
145                 150                 155                 160
```

```
Arg Cys His Phe Ile His Asn Pro Ser Glu Asp Leu Ala Ala Pro Gly
                165                 170                 175

His Pro Pro Val Leu Arg Gln Ser Ile Ser Phe Ser Gly Leu Pro Ser
            180                 185                 190

Gly Arg Arg Thr Ser Pro Pro Pro Gly Leu Ala Gly Pro Ser Leu
        195                 200                 205

Ser Ser Ser Ser Phe Ser Pro Ser Ser Ser Pro Pro Pro Gly Asp
    210                 215                 220

Leu Pro Leu Ser Pro Ser Ala Phe Ser Ala Ala Pro Gly Thr Pro Leu
225                 230                 235                 240

Ala Arg Arg Asp Pro Thr Pro Val Cys Cys Pro Ser Cys Arg Arg Ala
                245                 250                 255

Thr Pro Ile Ser Val Trp Gly Pro Leu Gly Gly Leu Val Arg Thr Pro
                260                 265                 270

Ser Val Gln Ser Leu Gly Ser Asp Pro Asp Glu Tyr Ala Ser Ser Gly
                275                 280                 285

Ser Ser Leu Gly Gly Ser Asp Ser Pro Val Phe Glu Ala Gly Val Phe
            290                 295                 300

Ala Pro Pro Gln Pro Val Ala Ala Pro Arg Arg Leu Pro Ile Phe Asn
305                 310                 315                 320

Arg Ile Ser Val Ser Glu
                325

<210> SEQ ID NO 3
<211> LENGTH: 1745
<212> TYPE: DNA
<213> ORGANISM: Homo sapiens

<400> SEQUENCE: 3
agcctgactt cagcgctccc actctcggcc gacacccctc atggccaacc gttacaccat      60
ggatctgact gccatctacg agagcctcct gtcgctgagc cctgacgtgc ccgtgccatc     120
cgaccatgga gggactgagt ccagcccagg ctggggctcc tcgggaccct ggagcctgag     180 ccccctccgac tccagcccgt ctggggtcac ctcccgcctg cctggccgct ccaccagcct     240
agtggagggc cgcagctgtg gctgggtgcc cccacccccct ggcttcgcac cgctggctcc     300
ccgcctgggc cctgagctgt caccctcacc cacttcgccc actgcaacct ccaccacccc     360
ctcgcgctac aagactgagc tatgtcggac cttctcagag agtgggcgct gccgctacgg     420
ggccaagtgc cagtttgccc atggcctggg cgagctgcgc caggccaatc gccaccccaa     480
atacaagacg gaactctgtc acaagttcta cctccagggc cgctgccct acggctctcg     540 ctgccacttc atccacaacc tagcgaaga cctggcggcc ccgggccacc tcctgtgct     600 tcgccagagc atcagcttct ccggcctgcc ctctggccgc ggacctcac caccaccacc     660 aggcctggcc ggcccttccc tgtcctccag ctccttctcg ccctccagct ccccaccacc     720
acctggggac cttccactgt cacccctctgc ctttctgct gcccctggca cccccctggc     780
tcgaagagac cccaccccag tctgttgccc ctcctgccga agggccactc ctatcagcgt     840
ctggggcccc ttgggtggcc tggttcggac cccctctgta cagtccctgg gatccgaccc     900
tgatgaatat gccagcagcg gcagcagcct gggggctct gactctcccg tcttcgaggc     960
gggagttttt gcaccaccc agccgtggc agcccccgg cgactccca tcttcaatcg    1020 catctctgtt tctgagtgac aaagtgactg cccggtcaga tcagctggat tcagcgggg    1080 agccacgtct cttgcactgt ggtctctgca tggaccccag ggctgtgggg acttgggga    1140
```

-continued

```
cagtaatcaa gtaatcccct tttccagaat gcattaaccc actcccctga cctcacgctg    1200
gggcaggtcc ccaagtgtgc aagctcagta ttcatgatgg tgggggatgg agtgtcttcc    1260
gaggttcttg ggggaaaaaa aattgtagca tatttaaggg aggcaatgaa ccctctcccc    1320
cacctcttcc ctgcccaaat ctgtctccta gaatcttatg tgctgtgaat aataggcctt    1380
cactgcccct ccagttttta tagacctgag gttccagtgt ctcctggtaa ctggaacctc    1440
tcctgagggg gaatcctggt gctcaaatta ccctccaaaa gcaagtagcc aaagccgttg    1500
ccaaacccca cccataaatc aatgggccct ttatttatga cgactttatt tattctaata    1560 tgatttata gtatttatat atattgggtc gtctgcttcc cttgtatttt tcttcctttt    1620
tttgtaatat tgaaaacgac gatataatta ttataagtag actataatat atttagtaat    1680
atatattatt accttaaaag tctatttttg tgttttgggc attttttaaat aaacaatctg    1740 agtgt                                                                1745
```

<210> SEQ ID NO 4
<211> LENGTH: 20
<212> TYPE: DNA
<213> ORGANISM: Artificial Sequence
<220> FEATURE:
<223> OTHER INFORMATION: Synthetic Sense primer

<400> SEQUENCE: 4
ccactctcgg ccgacacccc                                                20

<210> SEQ ID NO 5
<211> LENGTH: 22
<212> TYPE: DNA
<213> ORGANISM: Artificial Sequence
<220> FEATURE:
<223> OTHER INFORMATION: Synthetic Antisense primer

<400> SEQUENCE: 5
gtcactcaga aacagagatg cg                                             22

<210> SEQ ID NO 6
<211> LENGTH: 19
<212> TYPE: DNA
<213> ORGANISM: Artificial Sequence
<220> FEATURE:
<223> OTHER INFORMATION: Synthetic Primer 103F

<400> SEQUENCE: 6
cgaccatgga gggactgag                                                 19

<210> SEQ ID NO 7
<211> LENGTH: 20
<212> TYPE: DNA
<213> ORGANISM: Artificial Sequence
<220> FEATURE:
<223> OTHER INFORMATION: Synthetic Primer 103R

<400> SEQUENCE: 7
gccctggagg tagaacttgt                                                20

<210> SEQ ID NO 8
<211> LENGTH: 13
<212> TYPE: DNA
<213> ORGANISM: Artificial Sequence
<220> FEATURE:
<223> OTHER INFORMATION: TTP coding region from MDA231 DNA

```
<400> SEQUENCE: 8
tcgcgctaca aga                                                    13

<210> SEQ ID NO 9
<211> LENGTH: 13
<212> TYPE: DNA
<213> ORGANISM: Artificial Sequence
<220> FEATURE:
<223> OTHER INFORMATION: TTP coding region from Hs578T cDNA

<400> SEQUENCE: 9
tcgcgttaca aga                                                    13

<210> SEQ ID NO 10
<211> LENGTH: 13
<212> TYPE: DNA
<213> ORGANISM: Artificial Sequence
<220> FEATURE:
<223> OTHER INFORMATION: TTP coding region from Hs578T DNA

<400> SEQUENCE: 10
tcgcgttaca aga                                                    13
```

METHOD FOR PREDICTING THE RESPONSE TO TREATMENT WITH AN HER2-BLOCKING AGENT

This application includes an electronic CRF copy of a Substitute Sequence listing, identified as "2015-05-19 3493-0420PUS1_ST 25.txt", created on May 19, 2015 and having a size of 17.5 kb. The entire contents of the material in the ASCII text file are hereby incorporated by reference.

The present invention relates to the field of prediction of the response of a patient to anti-cancer treatment. In particular, it relates to a method for predicting the response of a patient to treatment with an HER2-blocking agent.

The membrane receptor HER2 (human epidermal growth factor receptor 2) is a member of the epidermal growth factor receptor (EGFR) family. The 185 kDa HER2 oncoprotein consists of an extracellular domain, a transmembrane domain and an intracellular region having intrinsic tyrosine kinase activity (Bargman et al., 1986; Yamamoto et al. 1986). The HER2 transmembrane glycoprotein thus has tyrosine kinase activity leading to activation of transcription of genes regulating progression of the cell cycle.

Overexpression of HER2 protein has been identified in various cancers, called "HER2-positive" cancers, including in particular breast (principal cause of death of women suffering from cancer worldwide), ovary, colon, pancreas, prostate and stomach cancers. This overexpression is correlated with greater tumor aggressiveness, increased risk of recurrence and poor prognosis. In particular, studies have shown that the gene coding for HER2 protein was amplified by a factor of 2 to more than 20 in 30% of cases of invasive breast cancers and that this amplification is associated with a very poor prognosis for patient survival (Slamon et al., 1987).

However, the development of therapeutic antibodies directed against HER2, in particular the monoclonal antibody trastuzumab (marketed notably under the name Herceptin®, F. Hoffmann-La Roche Ltd, Basel, Switzerland and Genentech, Inc., South San Francisco, Calif.) has made it possible to change this prognosis (De Laurentiis et al., 2005). Thus, treating patients suffering from HER2-positive breast cancer with trastuzumab has made it possible to very significantly increase the overall survival rate of these patients (Gianni et al., 2011).

Although trastuzumab constitutes remarkable progress in the treatment of HER2-positive breast cancer, this antibody is unfortunately not effective for all patients. Indeed, certain patients are refractory or develop resistance to trastuzumab treatment, generally in the year following initiation of metastasis (Nahta et al., 2006).

Furthermore, this type of treatment has the disadvantage of being very expensive.

It is thus advantageous to have a reliable method for predicting the response of a patient to treatment with an HER2-blocking agent, in particular trastuzumab; such a method making it possible to adapt therapeutic treatment to each patient, to avoid possible side effects, to develop alternative therapies and to reduce health expenditures.

Methods aimed at predicting the response of a patient to treatment with an HER2-blocking agent, in particular trastuzumab, notably based on determining the expression of several genes, are known in the prior art.

For example, International Application WO 2009/150127 teaches a method for predicting the response of a patient to treatment with an HER2-blocking agent, comprised of determining the expression of at least 4 genes. In particular, the inventors of this Application identified an expression profile of 28 genes for predicting the response of a patient suffering from HER2-positive breast cancer to treatment with trastuzumab (Végran et al., 2009). However, such a method has certain disadvantages. For example, it requires analysis of the expression a large number of genes, which can be long and expensive. Furthermore, it requires the taking of a tumor sample from the patient, which can require a surgical procedure, risking promoting the development of malignant cells in nearby tissues, leaving after-effects (scars, etc.) or being painful.

Certain methods are based on detecting the level of HER2 protein in circulating cancer cells, such as illustrated in International Application WO 2006/041959. However, these methods can be difficult to implement and require particular expensive equipment presently not present in all medical centers.

Thus, the methods known in the prior art can in particular have the disadvantages of being difficult to implement, expensive and/or not very reliable.

There thus remains a need for methods for predicting the response of a patient to treatment with an HER2-blocking agent, with improved characteristics and conditions of application, notably in terms of economics, simplicity, speed and/or reliability, which can be used in the greatest number of medical centers; these methods in particular enabling clinicians to make the most appropriate therapeutic decision for each patient suffering from HER2-related pathology, in particular HER2-positive cancer, notably HER2-positive breast cancer.

Surprisingly, the inventors have now identified a silent polymorphism in the genecoding for the tristetraprolin protein (TTP), the presence of which is correlated with reduced translation of this protein and with lack of response to treatment with an HER2-blocking agent.

This correlation is particularly unexpected. Indeed, studies have shown that tristetraprolin protein negatively regulates expression of the mRNA of various genes overexpressed in various cancers, by decreasing their half-life. These mRNA are members of the ARE-mRNA family (mRNA containing AU-rich elements in the 3' untranslated region, or 3'UTR) and are the products of genes involved in various cell control processes, such as cell division, apoptosis and angiogenesis. Deregulation of the expression of these ARE-mRNA, namely overexpression of these ARE-mRNA, leads to an oncogenic phenotype.

Thus, in the case of breast cancer, target mRNA regulated by the tristetraprolin protein have been identified as being ARE-mRNA, products of various genes including uPA, MMPA and uPAR (Al-Souhibani et al., 2010).

However, although HER2 overexpression has been shown in various cancers (in particular breast cancer) and HER2 is involved in progression of the cell cycle, the mRNA coding for HER2 is not a member of the ARE-mRNA family and is even less of a target of the tristetraprolin protein.

Thus, according to a first aspect, the invention relates to an in vitro or ex vivo method for predicting the response of a patient to treatment with at least one HER2-blocking agent, said method including the steps of:
i) identifying the nucleotide at the rs3746083 polymorphic site, for at least one allele (at least one copy), in particular both alleles (both copies) of the gene coding for the tristetraprolin protein in a biological sample from said patient; and/or
ii) determining the level of tristetraprolin protein in a biological sample from said patient.

The method of prediction of the invention has in particular the following advantages:

It is simple and fast. In particular, step i) has the advantage of not requiring the taking of a tumor sample from the patient and thus avoiding the various risks and problems related to performing a biopsy. Indeed, it can be implemented from an ordinary 5 to 10 ml blood sample from a patient by simple molecular biology techniques. It simply requires a standard molecular biology platform already present in many medical centers. Furthermore, step i) has the advantage of providing a result that is particularly easy to analyze. Step ii) has the advantage of requiring only the analysis of the level of only one protein;

It is reliable, reproducible and inexpensive.

The implementation of steps i) and ii) in the method of the invention has the advantage of optimizing the prediction of the response of a patient to treatment with at least one HER2-blocking agent, in particular trastuzumab.

Figure 1A:
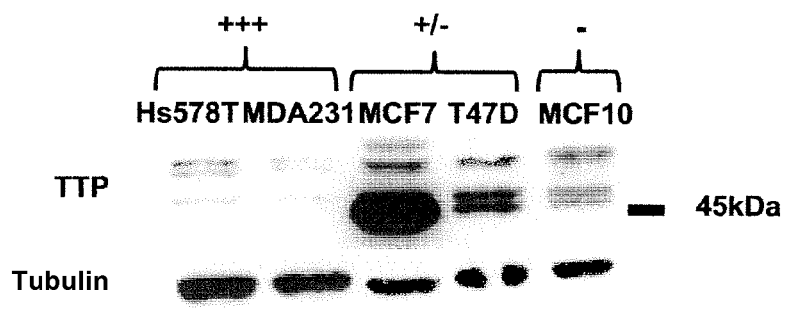
FIG. 1(A-C) is a view showing the expression of tristetraprolin (TTP), vascular endothelial growth factor and interleukin-8 (IL8) in breast cancer cell lines.

In order to enable better understanding of the present invention, certain definitions are provided. Unless specifically indicated, the other technical terms used in the present Application should be interpreted in their usual sense.

In the context of the present invention, "HER2" refers to the 185 KDa oncoprotein, also called erbB-2, ERBB2 or NEU. In particular, HER2 has the amino acids sequence SEQ ID NO: 1 (NCBI reference: NP_004439.2).

In the context of the present invention, "HER2-blocking agent" refers to any molecule (such as nucleic acid molecules, including DNA molecules, RNA molecules such as interfering RNA molecules, peptides, proteins, antibodies, antibody fragments, etc.) significantly inhibiting HER2 functions, in particular significantly inhibiting HER2 tyrosine kinase activity and/or HER2 expression.

Significant inhibition of HER2 functions, in particular HER2 tyrosine kinase activity and/or HER2 expression, can correspond to a reduction of at least 10%, at least 15%, at least 20%, at least 25%, at least 30%, at least 35%, at least 40%, at least 45%, in particular of at least 50% of HER2 functions, in particular HER2 tyrosine kinase activity and/or HER2 expression, in relation to a control in the absence of an HER2-blocking agent.

Said HER2-blocking agent can bind to the extracellular domain of HER2, inhibit the homodimerization and/or heterodimerization of HER2, bind to the intracellular domain of HER2, inhibit the tyrosine kinase domain of HER2 and/or inhibit the expression of the gene coding for HER2, as described in the article by Chen et al. (2003).

In particular, said HER2-blocking agent can be selected from the group consisting of:
  antibodies directed against the HER2 extracellular domain, in particular trastuzumab (Herceptin®);
  antibodies directed against HER2 and inhibiting the homodimerization and/or heterodimerization of HER2, such as with HERS, in particular the monoclonal antibody pertuzumab (also called 2C4, Omnitarg®);
  anti-HER2 vaccines;
  inhibitors of HER2 tyrosine kinase activity, in particular emodin (3-methyl-1,6,8-trihydroxyanthraquinone), curcumin, OSI-774 (Tarceva®), ZD-1839 (Iressa®), CI-1033 and lapatinib (Tykerb®, GSK572016, GW572016; GlaxoSmithKline, Research Triangle Park, N.C., USA);
  intracellular single-chain antibodies directed against HER2, in particular directed against the HER2 extracellular domain. This type of antibody avoids the transit of HER2 through the endoplasmic reticulum;
  inhibitors of transcription of the gene coding for HER2, in particular the adenovirus E1A gene; and
  inhibitors of translation of the mRNA coding for HER2, such as antisense oligonucleotides and ribozymes;
  these various types of HER2-blocking agents being in particular illustrated in the article by Chen et al. (2003).

Said HER2-blocking agent can be identified according to techniques well-known to persons skilled in the art. For example, said HER2-blocking agent can be identified by a method comprised of:
  placing an agent to be tested in contact with a cell expressing HER2;
  growing said cell under HER2 expression conditions;
  determining HER2 functions and/or HER2 expression level;
  comparing HER2 functions, in particular HER2 tyrosine kinase activity and/or HER2 expression level in the presence and in the absence of said agent to be tested;
  the significant reduction of HER2 functions, in particular tyrosine kinase activity and/or HER2 expression level in the presence of said agent to be tested being indicative of the presence of an HER2-blocking agent.

In particular, said HER2-blocking agent is an antibody directed against HER2, directed in particular against the HER2 extracellular domain and/or inhibiting the homodimerization and/or heterodimerization of HER2, and particularly selected from the group comprised of trastuzumab (Herceptin®) and pertuzumab (also called 2C4, Omnitarg®), and more particularly trastuzumab.

As used in the present Application, the term "antibody" includes intact monoclonal and polyclonal antibodies, multispecific antibodies (bispecific antibodies, for example) formed of at least two intact antibodies, and antibody fragments (Fab', F'(ab)$_2$, Fv, single-chain antibodies, for example) insofar as they have the desired biological activity.

In the context of the present invention, "antibody directed against a protein" refers to any antibody that binds specifically to this protein.

Antibodies are said to "bind specifically" if: 1) they have a binding activity threshold, and/or 2) they do not significantly cross-react with related polypeptides. Persons skilled in the art, for example by Scatchard analysis (1949) or by surface plasmon resonance, can easily determine the binding affinity of an antibody.

In the context of the present invention, "tristetraprolin protein" refers to the protein also called ZFP36 (zinc finger protein 36) or TTP or G0S24 or GOS24 or TIS11 or NUP475 or RNF162A; member of the ARE-mRNA (mRNA containing AU-rich elements in the 3'UTR area) binding protein family. In particular, the tristetraprolin protein has the sequence SEQ ID NO: 2 (GenBank reference: AAA61240.1, NCBI reference: NP_003398.1).

In the context of the present invention, "rs3746083 polymorphic site" refers to position rs3746083 on the human genome in which a single-nucleotide polymorphism (SNP) exists. The nucleotides at the rs3746083 polymorphic site can be the nucleotides A, C, G or T, the ancestral nucleotide being a C nucleotide (NCBI references: NM_003407.2: 367C>A; NM_003407.2: 367C>G; NM_003407.2: 367C>T).

In particular, the nucleotide at the rs3746083 polymorphic site corresponds to the nucleotide at position 367 of the sequence SEQ ID NO: 3 (NCBI reference: NM_003407.2).

In particular, the nucleotide at the rs3746083 polymorphic site is the nucleotide at position 367 of the sequence SEQ ID NO: 3 (NCBI reference: NM_003407.2).

In the context of the present invention, "rs3746083 polymorphism" refers to the single-nucleotide polymorphism (SNP) located at position rs3746083 on the human genome. The alleles of the rs3746083 polymorphism can be the A, C, G or T alleles, the ancestral allele being the C allele (NCBI references: NM_003407.2: 367C>A; NM_003407.2: 367C>G; NM_003407.2: 367C>T). In particular, the rs3746083 polymorphism corresponds to the 367C>T polymorphism on the sequence SEQ ID NO: 3 (NCBI reference: NM_003407.2).

Step i) of identifying the nucleotide at the rs3746083 polymorphic site, for at least one allele (at least one copy), in particular both alleles (both copies), of the gene coding for the tristetraprolin protein in a biological sample from said patient can be implemented by any technique well-known to persons skilled in the art, such as by enzymatic digestion, sequencing, specific hybridization and/or specific amplification.

Sequencing can be carried out using well-known techniques, notably using automatic sequencers on genomic DNA, cDNA or RNA of the patient having the nucleotide at the rs3746083 polymorphic site.

Amplification can be carried out by various known techniques, using specific nucleic acid primers to amplify genomic DNA, cDNA or RNA of the patient having the nucleotide at the rs3746083 polymorphic site. In particular, such primers are capable of hybridizing specifically with parts of the genomic DNA, cDNA or RNA of the patient which flank the nucleotide at the rs3746083 polymorphic site.

As examples of amplification techniques, mention may be made of the polymerase chain reaction (PCR), strand displacement amplification (SDA), ligase chain reaction (LCR) and nucleic acid sequence-based amplification (NASBA). These techniques can be carried out using commercially-available reagents and protocols.

Methods of detection by hybridization are based on the formation of specific hybrids between the complementary nucleic acid sequences which are used to detect the polymorphism and the genomic DNA, cDNA or RNA of the patient having the nucleotide at the rs3746083 polymorphic site. In particular, a detection technique involves the use of a nucleic acid probe specific to the C allele, T allele, A allele or G allele of the rs3746083 polymorphism, followed by detection of the presence of a hybrid. The probe can be suspended or immobilized on a substrate or support, in particular on a chip. The probe is generally marked so as to facilitate the detection of hybrids; the markers can be fluorescent, chemiluminescent, radioactive or enzymatic markers, stains, or others.

The absence of a C nucleotide at the rs3746083 polymorphic site (absence of the C allele of the rs3746083 polymorphism) can be easily detected by enzymatic digestion with the restriction enzyme HhaI, preceded by amplification of the genomic DNA, cDNA or RNA of the patient having the nucleotide at the rs3746083 polymorphic site and optionally followed by sequencing of the amplified and digested fragments. Indeed, the absence of a C nucleotide at the rs3746083 polymorphic site (of the C allele of the rs3746083 polymorphism) removes the HhaI enzyme restriction site.

The evaluation of the results obtained in step i) makes it possible to predict the response of the patient to treatment with at least one HER2-blocking agent, in particular trastuzumab.

Thus, in the method of prediction of the invention, the absence of the C nucleotide at the rs3746083 polymorphic site, for at least one allele (at least one copy), in particular both alleles (both copies) of the gene coding for the tristetraprolin protein in a patient is indicative of a risk of no response by said patient to treatment with at least one HER2-blocking agent, in particular trastuzumab. Said patient is then predicted to be not responsive to said treatment.

Thus, in the method of prediction of the invention, presence of a T nucleotide at the rs3746083 polymorphic site, for at least one allele (at least one copy), in particular both alleles (both copies) of the gene coding for the tristetraprolin protein in a patient is indicative of a risk of no response by said patient to treatment with at least one HER2-blocking agent, in particular trastuzumab. Said patient is then predicted to be not responsive to said treatment.

Thus, in the method of prediction of the invention, the presence of a T nucleotide at the rs3746083 polymorphic site, for at least one allele (at least one copy), in particular both alleles (both copies) of the gene coding for the tristetraprolin protein in a patient, is indicative of a higher risk of no response by said patient to treatment with at least one HER2-blocking agent, in particular trastuzumab, in comparison with a patient lacking a T nucleotide at the rs3746083 polymorphic site, in particular in comparison with a patient in which both alleles (both copies) of the gene coding for the tristetraprolin protein contain a C nucleotide at the rs3746083 polymorphic site.

Thus, in the method of the invention, the identification of heterozygosity (T/C) at the rs3746083 polymorphic site in a patient (presence of a T nucleotide at the rs3746083 polymorphic site for one allele of the gene coding for the tristetraprolin protein, and presence of a C nucleotide at the rs3746083 polymorphic site for the other allele of the gene coding for the tristetraprolin protein) is indicative of a higher risk of no response by said patient to treatment with at least one HER2-blocking agent, in particular trastuzumab, in comparison with a patient having homozygosity (C/C) at the rs3746083 polymorphic site.

The patient having heterozygosity (T/C) at the rs3746083 polymorphic site is predicted to be not responsive to treatment with at least one HER2-blocking agent, in particular trastuzumab.

The patient having homozygosity (C/C) at the rs3746083 polymorphic site is predicted to be responsive to treatment with at least one HER2-blocking agent, in particular trastuzumab.

Thus, in the method of the invention, the patient is predicted to be responsive to treatment with at least one HER2-blocking agent, in particular trastuzumab, if the nucleotide at the rs3746083 polymorphic site is a C nucleotide for both alleles (both copies) of the gene coding for the tristetraprolin protein in said patient.

Said method of prediction of the invention can further include the following step:

assigning said patient to a no-response group if the nucleotide at the rs3746083 polymorphic site is not a C nucleotide for at least one allele (at least one copy), in particular both alleles (both copies) of the gene coding for the tristetraprolin protein, in particular if the nucleotide at the rs3746083 polymorphic site is a T nucleotide for at least one allele (at least one copy), in particular both alleles (both copies) of the gene coding for the tristetraprolin protein in said patient, or assigning said patient to a response group if the nucleotide at the rs3746083 polymorphic site is a C nucleotide for both alleles (both copies) of the gene coding for the tristetraprolin protein in said patient.

The method of the invention can include detection of at least one polymorphism (in particular a single-nucleotide polymorphism, or SNP) in linkage disequilibrium with the rs3746083 polymorphism. Such polymorphisms in linkage disequilibrium with the rs3746083 polymorphism can be identified by any technique well-known to persons skilled in the art.

For example, the identification of polymorphism in linkage disequilibrium with the rs3746083 polymorphism can include: (a) amplification of a fragment of the genomic region including or surrounding the rs3746083 polymorphism of a plurality of patients; (b) identification of second polymorphisms in the genomic region including or flanking said rs3746083 polymorphism; (c) analysis of the linkage disequilibrium between said rs3746083 polymorphism and said second polymorphisms, and (d) selection of said second polymorphisms in linkage disequilibrium with said rs3746083 polymorphism.

In the context of the present invention, "biological sample" refers to any biological sample from a patient. This term includes any biological fluid, sample of tissues, cells or organs, biopsies, or any tissue or cell culture derived therefrom.

In particular, said biological sample can be a "pathological" biological sample (characteristic of pathology), such as a sample of pathological tissue or cells, in particular cancerous and more particularly HER2-positive.

The term "biological sample" also includes samples that have been manipulated, in particular treated by reagents, by solubilization or by enrichment of certain elements. Thus, the biological sample can be treated before use in the method of the invention, for example, in order to isolate and/or concentrate nucleic acids or proteins, according to all techniques well-known to persons skilled in the art. As examples of such techniques, mention may be made of the techniques of lysis (for example, mechanical, physical, chemical, etc.), cell concentration and nucleic acid dilution. Nucleic acids can also be treated with enzymes or other chemical or physical treatments to produce nucleic acid fragments.

In particular, said biological sample that can be used in step i) includes nucleic acids, particularly genomic DNA of said patient, and can be selected from the group comprised of: a sample of blood, such as a whole blood, serum or plasma, a saliva sample, a seminal liquid sample and a urine sample.

In particular, said biological sample that can be used in step ii) includes proteins from said patient and can be selected from the group comprised of: a blood sample, a sample of tissue or cells, in particular breast tissue or cells, particularly cancer tissue or cells and more particularly HER2-positive cancer tissue or cells.

The term "patient" as used in the present Application refers to any individual, patient, in particular any human being for whom the prediction, prognosis, diagnosis or therapy is desired. In particular, the patient is a woman and particularly a woman suffering from HER2-positive breast cancer.

Said patient can be suffering from pathology and/or disorders for which treatment with at least one HER2-blocking agent is beneficial, including benign and malignant tumors. In particular, said patient is suffering from an HER2-related pathology and/or disorder, particularly HER2-positive pathology and more particularly HER2-positive cancer.

In the context of the present invention, the expression "HER2-related pathology and/or disorder" refers to any pathology and/or disorder for which treatment with at least one HER2-blocking agent is beneficial.

In the context of the present invention, the expression "HER2-positive pathology, in particular HER2-positive cancer" refers to any pathology, in particular any cancer, in which the HER2 protein is overexpressed, that is, has an abnormal level of expression in a cell, tissue or organ of the patient suffering from this pathology in relation to the level of expression in a cell, tissue or organ of an patient that is healthy or is not suffering from this pathology.

HER2-positive cancers include in particular breast, ovary, colon, pancreas, prostate, stomach, endometrium cancers and non-small-cell lung cancers (NSCLC).

Patients suffering from HER2-positive pathology, in particular HER2-positive cancer, can be identified using any technique well-known to persons skilled in the art such as electrophoretic and immunological techniques using antibodies directed against HER2 or chromogenic in situ hybridization (CISH®) techniques to detect amplification of the gene coding for HER2, in particular on fixed, paraffin-embedded tissue sections. For example, mention may be made of the Zymed Spot-Light® HER2CISH Kit™ (marketed by Zymed Laboratories®) for detecting amplification of the HER2 gene in sections of formalin-fixed, paraffin-embedded (FFPE) tissue, by chromogenic in situ hybridization (CISH™).

The method of the invention makes it possible to distinguish patients that respond to treatment with at least one HER2-blocking agent, in particular trastuzumab, from patients that do not respond.

In the context of the present invention, "patient responding to treatment with at least one HER2-blocking agent" refers to any patient that shows clinically significant relief of an HER2-related pathology and/or disorder, in particular HER2-positive pathology, more particularly HER2-positive cancer and still more particularly HER2-positive breast cancer, when treated with said agent, according to Response Evaluation Criteria in Solid Tumors (RECIST).

In the context of the present invention, "patient not responding to treatment with at least one HER2-blocking agent" refers to any patient that does not show clinically significant relief of an HER2-related pathology and/or disorder, in particular HER2-positive pathology, more particularly HER2-positive cancer and still more particularly HER2-positive breast cancer, when treated with said agent, according to Response Evaluation Criteria in Solid Tumors (RECIST).

Step ii) of determining the level of tristetraprolin protein in a biological sample from a patient can be implemented by any technique well-known to persons skilled in the art.

Such techniques can include placing a biological sample in contact with a binding agent capable of interacting selectively with the tristetraprolin protein likely to be present in the biological sample.

The binding agent can be an antibody, in particular a polyclonal or monoclonal antibody, and particularly a monoclonal antibody directed against the tristetraprolin protein.

Thus, the level of tristetraprolin protein can be determined by means of electrophoretic and immunological techniques using antibodies directed against the tristetraprolin protein. As examples, mention may be made of Western blots, enzymatic tests such as ELISA, tests of the biotin/avidin type, radioimmunological tests, immunoelectrophoresis and immunoprecipitation. These techniques generally include markers for detecting the formation of a complex between the tristetraprolin protein and the binding agent, in particular between the antigen and the antibody or antibodies which reacted with it; said markers being able to be fluorescent, chemiluminescent, radioactive or enzymatic markers, stains or others.

Said method of prediction of the invention can further include the step of:

iii) comparing the level of tristetraprolin protein in a biological sample from said patient determined in step ii) with at least one reference value.

This step iii) helps determine whether a patient is responsive or non-responsive to treatment with at least one HER2-blocking agent, in particular trastuzumab.

Said reference value can be in particular, in a non-limiting manner:
- a reference threshold value;
- the average value of the level of tristetraprolin protein determined in healthy tissue, said healthy tissue neighboring the tumor tissue from which the level of tristetraprolin protein was determined in step ii);
- the average value of the level of tristetraprolin protein, determined in an equivalent biological sample, for a group of patients responsive to treatment with at least one HER2-blocking agent, in particular trastuzumab; or
- the average value of the level of tristetraprolin protein, determined in an equivalent biological sample, for a group of patients not responsive to treatment with at least one HER2-blocking agent, in particular trastuzumab.

In the context of the present invention, "equivalent biological sample" refers to any biological sample corresponding physiologically to that of step ii). For example, when the biological sample of step ii) is a sample of cancerous breast tissue, the equivalent biological sample can be a breast tissue sample, preferably from the same region as that of step ii).

Thus, for example, when the level of tristetraprolin protein determined in step ii) is significantly lower than the reference value, said reference value corresponding to the average value of the level of tristetraprolin protein determined in healthy tissue, said healthy tissue neighboring the tumor tissue from which the level of tristetraprolin protein was determined in step ii), then the patient is predicted to be not responsive to said at least one HER2-blocking agent, in particular trastuzumab.

Thus, for example, when the level of tristetraprolin protein determined in step ii) is greater than or equal to the reference value, said reference value corresponding to the average value of the level of tristetraprolin protein determined in healthy tissue, said healthy tissue neighboring the tumor tissue from which the level of tristetraprolin protein was determined in step ii), then the patient is predicted to be responsive to said at least one HER2-blocking agent, in particular trastuzumab.

Thus, for example, when the level of tristetraprolin protein determined in step ii) is significantly lower than the reference value, said reference value corresponding to the average value of the level of tristetraprolin protein, determined in an equivalent biological sample, for a group of patients responsive to treatment with at least one HER2-blocking agent, in particular trastuzumab, then the patient is predicted to be not responsive to said at least one HER2-blocking agent, in particular trastuzumab.

Thus, for example, when the level of tristetraprolin protein determined in step ii) is greater than or equal to the reference value, said reference value corresponding to the average value of the level of tristetraprolin protein, determined in an equivalent biological sample, for a group of patients responsive to treatment with at least one HER2-blocking agent, in particular trastuzumab, then the patient is predicted to be responsive to said at least one HER2-blocking agent, in particular trastuzumab.

For example, when the level of tristetraprolin protein determined in step ii) is significantly higher than the reference value, said reference value corresponding to the average value of the level of tristetraprolin protein, determined in an equivalent biological sample, for a group of patients not responsive to treatment with at least one HER2-blocking agent, in particular trastuzumab, then the patient is predicted to be responsive to said at least one HER2-blocking agent, in particular trastuzumab.

For example, when the level of tristetraprolin protein determined in step ii) is equal to or less than the reference value, said reference value corresponding to the average value of the level of tristetraprolin protein, determined in an equivalent biological sample, for a group of patients not responsive to treatment with at least one HER2-blocking agent, in particular trastuzumab, then the patient is predicted to be not responsive to said at least one HER2-blocking agent, in particular trastuzumab.

A level of tristetraprolin protein significantly higher than the reference value can correspond to a level higher than at least 15%, at least 20%, at least 25%, at least 30%, at least 35% in relation to the reference value.

A level of tristetraprolin protein significantly lower than the reference value can correspond to a level lower than at least 15%, at least 20%, at least 25%, at least 30%, at least 35% in relation to the reference value.

The method of the invention can also include determining the level of a control protein in a biological sample from said patient. Said control protein can in particular be a protein whose level is constant in patients responsive and not responsive to treatment with at least one HER2-blocking agent, in particular trastuzumab.

The method of prediction of the invention can also include a step of determining at least one additional parameter useful for the prediction, in particular from a biological sample from said patient. The expression "additional parameter useful for the prediction" refers to any parameter that cannot be used alone for the prediction but that has been described as, for example, showing significantly different values between a patient that responds and a patient that does not respond to treatment with at least one HER2-blocking agent and that can be useful to confirm the prediction determined by the method of the invention. One such additional parameter useful for the prediction can be:

the expression level of at least one gene chosen from the group consisting of GPR22 (G protein-coupled receptor 22, in particular GenBank reference: NM_005295), PEX19 (peroxisomal biogenesis factor 19, in particular GenBank reference: NM_002857), GRHL2 (grainyhead-like 2, in particular GenBank reference: NM_024915) and DERL1 (Derlin 1, in particular GenBank reference: NM_024295), the gene coding for HER2 (in particular GenBank reference: NM_004448).

Said method of prediction of the invention can further include the step of:

iv) predicting the response of said patient to treatment with at least one HER2-blocking agent, in particular trastuzumab, by evaluating the results obtained in step i) and/or step ii).

According to another aspect, the invention relates to an HER2-blocking agent for use as a drug for treating an HER2-related pathology and/or disorder, in particular HER2-positive pathology, more particularly HER2-positive cancer and still more particularly HER2-positive breast cancer in a patient, said patient being predicted to be responsive to treatment with said HER2-blocking agent by the method of prediction of the invention.

The present invention also relates to the use of an HER2-blocking agent for manufacturing a drug for treating an HER2-related pathology and/or disorder, in particular HER2-positive pathology, more particularly HER2-positive cancer and still more particularly HER2-positive breast cancer in a patient, said patient being predicted to be responsive to treatment with said HER2-blocking agent by the method of prediction of the invention.

The present invention also relates to a method for treating a patient suffering from an HER2-related pathology and/or disorder, in particular HER2-positive pathology, more particularly HER2-positive cancer and still more particularly HER2-positive breast cancer, said method including the following steps:

a) predicting the response of the patient to treatment with at least one HER2-blocking agent by implementing the method of prediction of the invention; and
b) administering a therapeutic quantity of an HER2-blocking agent to said patient predicted to be responsive to treatment with at least one HER2-blocking agent in step a).

In the context of the present invention, "therapeutic quantity" refers to an active and nontoxic quantity of an HER2-blocking agent.

These therapeutic quantities can be determined by persons skilled in the art by routine tests, including evaluation of the effect of administration of at least one HER2-blocking agent on the HER2-related pathologies and/or disorders sought to be treated by administration of said HER2-blocking agent, in particular on HER2-positive cancer and particularly on HER2-positive breast cancer.

For example, these tests can be implemented by analysis of both the quantitative and the qualitative effect of administration of various quantities of said HER2-blocking agent (in particular trastuzumab) on a set of markers (biological and/or clinical) characteristic of these HER2-related pathologies and/or disorders, in particular from at least one biological sample from at least one patient.

The present invention also relates to a product including:
at least one HER2-blocking agent and
at least one other agent for treating an HER2-related pathology and/or disorder, in particular HER2-positive pathology, more particularly HER2-positive cancer and still more particularly HER2-positive breast cancer,
as a combination product for simultaneous, separate or sequential use for treating an HER2-related pathology and/or disorder, in particular HER2-positive pathology, more particularly HER2-positive cancer and more particularly HER2-positive breast cancer in a patient, said patient being predicted to be responsive to treatment with said HER2-blocking agent by the method of prediction of the invention.

The present invention also relates to the use of:
at least one HER2-blocking agent and
at least one other agent for treating an HER2-related pathology and/or disorder, in particular HER2-positive pathology, more particularly HER2-positive cancer and still more particularly HER2-positive breast cancer,
for preparing a combination product for simultaneous, separate or sequential use for treating an HER2-related pathology and/or disorder, in particular HER2-positive pathology, more particularly HER2-positive cancer and more particularly HER2-positive breast cancer in a patient, said patient being predicted to be responsive to treatment with said HER2-blocking agent by the method of prediction of the invention.

In the context of the present invention, "agent for treating an HER2-related pathology and/or disorder" refers to any compound for treating an HER2-related pathology and/or disorder.

As examples, said other agent for treating an HER2-related pathology and/or disorder, in particular HER2-positive pathology, more particularly HER2-positive cancer and still more particularly HER2-positive breast cancer, can be:
a chemotherapy agent, such as, in particular in the case of breast cancer, taxanes (in particular docetaxel or Taxotere®), doxorubicin, 5-fluorouracil, epirubicin or cyclophosphamide,
a hormone therapy agent, such as, in particular in the case of breast cancer, tamoxifen, or
a radiotherapy agent.

Said HER2-blocking agent can be present in the drugs and combination products of the invention in a therapeutic quantity.

Said HER2-blocking agent and said other agent for treating an HER2-related pathology and/or disorder can be present in the combination products of the invention in a molar ratio of 100/1 to 1/100.

The drugs and combination products of the invention can be administered by various routes, in particular according to the type of HER2-blocking agent. As examples of administration routes that can be used for the drugs and combination products of the invention, mention may be made of the oral, rectal, cutaneous, pulmonary, nasal, sublingual and parenteral routes.

The drugs and combination products according to the invention can further include a pharmaceutically acceptable carrier.

In the context of the present invention, "pharmaceutically acceptable carrier" refers to any material appropriate for use in a medicinal product.

As examples of a pharmaceutically acceptable carrier, mention may be made of lactose, starch (optionally modified), cellulose, hydroxypropyl cellulose, hydroxypropylmethyl cellulose, mannitol, sorbitol, xylitol, dextrose, calcium sulfate, calcium phosphate, calcium lactate, dextrates, inositol, calcium carbonate, glycine, bentonite, polyvinylpyrrolidone and mixtures thereof.

The drugs and combination products of the invention can include a pharmaceutically acceptable carrier content of 5% to 99% by weight, notably 10% to 90% by weight and in particular 20% to 75% by weight in relation to the total weight of the drugs or combination products of the invention.

According to another aspect, the invention has as an object a kit for predicting the response of a patient to treatment with at least one HER2-blocking agent including:
means of identifying the nucleotide at the rs3746083 polymorphic site; and/or
means of determining the level of tristetraprolin protein; and optionally
instructions for using said means for predicting the response of a patient to treatment with at least one HER2-blocking agent.

The means of identifying the nucleotide at the rs3746083 polymorphic site can be nucleic acid primers and/or probes for identifying the nucleotide at the rs3746083 polymorphic site by sequencing, amplification and/or hybridization.

In particular, the means of identifying the nucleotide at the rs3746083 polymorphic site can be selected from the group comprised of:
specific primers and reagents for sequencing the genomic DNA, cDNA or RNA of a patient having the nucleotide at the rs3746083 polymorphic site;
specific primers and reagents for amplifying the genomic DNA, cDNA or RNA of a patient having the nucleotide at the rs3746083 polymorphic site. In particular, such nucleic acid primers are capable of hybridizing specifically with parts of the genomic DNA, cDNA or RNA of a patient which flank the nucleotide at the rs3746083 polymorphic site;
specific nucleic acid probes for the C allele, T allele, A allele and G allele of the polymorphism located at position rs3746083 on the human genome and reagents for detecting the formation of specific hybrids between the complementary nucleic acid sequences used to detect the polymorphism.

In particular, the means of determining the level of tristetraprolin protein can be antibodies directed against the tristetraprolin protein, in particular able to be used in an enzyme-linked immunosorbent assay (ELISA) or radioimmunoassay (RIA).

The prediction kit of the invention can further include additional elements such as buffers, reagents, markers and control samples.

The instructions for using said means for predicting the response of a patient to treatment with at least one HER2-blocking agent make it possible in particular to interpret the results obtained after identification of the nucleotide at the rs3746083 polymorphic site and/or determining the level of tristetraprolin protein in a biological sample from a patient.

For example, said instructions can indicate that the absence of the C nucleotide at the rs3746083 polymorphic site, for at least one allele (at least one copy), in particular both alleles (both copies) of the gene coding for the tristetraprolin protein in a patient is indicative of a risk of no response by said patient to treatment with at least one HER2-blocking agent, in particular trastuzumab. Said patient is then predicted to be not responsive to said treatment.

According to another aspect, the present invention relates to an in vitro or ex vivo method of prognosis or diagnosis of cancer, in particular of cancer with a poor prognosis, in a patient including:
α) identifying the nucleotide at the rs3746083 polymorphic site, for at least one allele (at least one copy), in particular both alleles (both copies) of the gene coding for the tristetraprolin protein in a biological sample from said patient.

Said cancer can be any cancer in which the tristetraprolin protein is underexpressed, that is, has an abnormal level of expression in a cell, tissue or organ of the patient suffering from this cancer in relation to the level of expression in a cell, tissue or organ of a patient that is healthy or is not suffering from this cancer, as illustrated in the articles by Brennan et al. (2009).

In particular, said cancer can be included in the group comprising lung, breast, uterus, ovary, vulva, prostate, testicles, trachea, thyroid, liver, stomach, intestine, colon, rectum, pancreas, kidney, bladder and skin cancers, particularly thyroid, lung, ovary, uterus and breast cancers, adenoma and adenocarcinoma and more particularly breast cancer.

According to a particular embodiment of the method of prognosis or diagnosis of the invention, said cancer is a breast cancer with a poor prognosis.

In the method of prognosis or diagnosis of the invention, the absence of the C nucleotide at the rs3746083 polymorphic site, for at least one allele (at least one copy), in particular both alleles (both copies) of the gene coding for the tristetraprolin protein is indicative of risk that the patient is suffering from cancer, in particular cancer with a poor prognosis and particularly breast cancer with a poor prognosis.

In the method of prognosis or diagnosis of the invention, the presence of a T nucleotide at the rs3746083 polymorphic site, for at least one allele (at least one copy), in particular both alleles (both copies) of the gene coding for the tristetraprolin protein is indicative of risk that the patient is suffering from cancer, in particular cancer with a poor prognosis and particularly breast cancer with a poor prognosis.

Thus, in the method of the invention, the identification of heterozygosity (T/C) at the rs3746083 polymorphic site in a patient (presence of a T nucleotide at the rs3746083 polymorphic site for one allele of the gene coding for the tristetraprolin protein, and presence of a C nucleotide at the rs3746083 polymorphic site for the other allele of the gene coding for the tristetraprolin protein) is indicative of risk that the patient is suffering from cancer, in particular cancer with a poor prognosis and particularly breast cancer with a poor prognosis.

The method of prognosis or diagnosis of the invention has in particular the following advantages:
It is simple and fast. Step α) has the advantage of not requiring the taking of a tumor sample from the patient and of thus avoiding the various risks and problems related to performing a biopsy. For example, it can be implemented from an ordinary 5 to 10 ml blood sample from a patient by simple molecular biology techniques. It requires a standard molecular biology platform already present in many hospitals. Furthermore, step α) has the advantage of providing a result that is particularly easy to analyze;
It is reliable, reproducible and inexpensive.

The method of prognosis or diagnosis of the invention can also include a step of determining at least one additional parameter useful for the prognosis or diagnosis, in particular from a biological sample from said patient. The expression "additional parameter useful for the prognosis or diagnosis" refers to any parameter that cannot be used alone for the prognosis or diagnosis but that has been described as, for example, showing significantly different values between a patient suffering from cancer and a patient not suffering from cancer and that can be useful to confirm the prognosis or diagnosis determined by the method of the invention. One such additional parameter useful for the prognosis or diagnosis can be:

the expression level of at least one gene whose expression is modulated in a patient suffering from said cancer, such as the gene coding for HER2 in the case of HER2-positive cancers.

The present invention also relates to a method for treating a patient suffering from cancer, in particular with a poor prognosis, including the following steps:

1) the prognosis or diagnosis of cancer in said patient by implementing the method of prognosis or diagnosis of the invention;

2) the administration of a therapeutic quantity of an anti-cancer agent to said patient diagnosed as suffering from cancer, in particular with a poor prognosis, in step 1).

According to the invention, "anti-cancer agent" refers to any compound for treating cancer and/or a cancer-related disorder. For example, said anti-cancer agent can be:

a chemotherapy agent, such as, in particular in the case of breast cancer, taxanes (in particular docetaxel or Taxotere®), doxorubicin, 5-fluorouracil, epirubicin or cyclophosphamide, a hormone therapy agent, such as, in particular in the case of breast cancer, tamoxifen, or a radiotherapy agent.

In particular, said anti-cancer agent is appropriate to the cancer diagnosed in said patient. For example, when the patient is suffering from HER2-positive breast cancer, said agent can be tamoxifen, docetaxel, etc.

According to another aspect, the invention relates to a kit for prognosis or diagnosis of cancer, in particular cancer with a poor prognosis, in a patient including:

means of identifying the nucleotide at the rs3746083 polymorphic site; and optionally instructions for using said means of establishing a prognosis or diagnosis of cancer, in particular cancer with a poor prognosis, in a patient.

The means of identifying the nucleotide at the rs3746083 polymorphic site can be nucleic acid primers and/or probes for identifying the nucleotide at the rs3746083 polymorphic site by sequencing, amplification and/or hybridization.

In particular, the means of identifying the nucleotide at the rs3746083 polymorphic site can be selected from the group comprised of:

specific primers and reagents for sequencing the genomic DNA, cDNA or RNA of a patient having the nucleotide at the rs3746083 polymorphic site;

specific primers and reagents for amplifying the genomic DNA, cDNA or RNA of a patient having the nucleotide at the rs3746083 polymorphic site. In particular, such nucleic acid primers are capable of hybridizing specifically with parts of the genomic DNA, cDNA or RNA of a patient which flank the nucleotide at the rs3746083 polymorphic site;

specific nucleic acid probes for the C allele, T allele, A allele and G allele of the polymorphism located at position rs3746083 on the human genome and reagents for detecting the formation of specific hybrids between the complementary nucleic acid sequences used to detect the polymorphism.

Said instructions for using said means of establishing a prognosis or diagnosis of cancer, in particular cancer with a poor prognosis, in a patient, make it possible in particular to interpret the results obtained after identification of the nucleotide at the rs3746083 polymorphic site.

For example, said instructions can indicate that the absence of the C nucleotide at the rs3746083 polymorphic site, for at least one allele (at least one copy), in particular both alleles (both copies) of the gene coding for the tristetraprolin protein is indicative of risk that the patient is suffering from cancer, in particular cancer with a poor prognosis.

Other advantages and characteristic of the invention will be apparent from the following examples.

These examples are given for purposes of illustration and are non-limiting.

FIG. 1 (A-C) represents the expression of TTP (tristetraprolin), VEGF (vascular endothelial growth factor) and IL8 (interleukin-8) in breast cancer cell lines. (A). Immunoblot of total TTP proteins in breast cancer lysates and in an immortalized breast cell line. (+++) Very aggressive breast cancer cell lines; (+/−) non-aggressive breast cancer cell lines; (−) non-tumoral breast cell line. (B) and (C) level of mRNA and secreted proteins VEGF and IL8 determined by qPCR and ELISA, respectively.

FIG. 2 (A-B) represents TTP-MDA231 inducible clones. (A) Various levels of TTP protein induction in three clones (low levels of TTP=PA15, high levels of TTP=PA1 and PA48) after removal of tetracycline. (B) Quantitative PCR of total quantities of VEGF and IL8 mRNA in TTP-MDA231 clones; *=p<0.05, **=p<0.01.

FIG. 3 (A-C) represents stable MCF7 clones obtained by transfection of shCTRL, sh62-TTP1 and sh65-TTP2 sequences. (A) Quantitative PCR of total TTP mRNA levels in three different clones. (B) Corresponding TTP protein level detected by immunoblot. (C) Quantitative PCR of VEGF and IL8 mRNA levels in the three clones. *=p<0.05, **=p<0.01.

FIG. 4 (A-C) represents the effect of TTP expression on the proliferation of inducible MDA231-TTP clones and stable shTTP-MCF7 clones. (A) Proliferation test of inducible TTP-MDA231 clones PA1 and PA15 in the presence or absence of tetracycline. TTP expression levels after induction are indicated (TTP+++=high levels and TTP+=low level. (B) Cell morphology. (C) Proliferation test of two stable shTTP-MCF7 clones in relation to shCTRL.

FIG. 5 (A-B) represents the comparative expression of TTP in breast cancer cell lines. (A) Protein extracts of breast cancer and HEK293 cell lines analyzed by immunoblot. (B) Corresponding mRNA levels in the same cell lines, quantified by quantitative PCR.

Figure 6A:
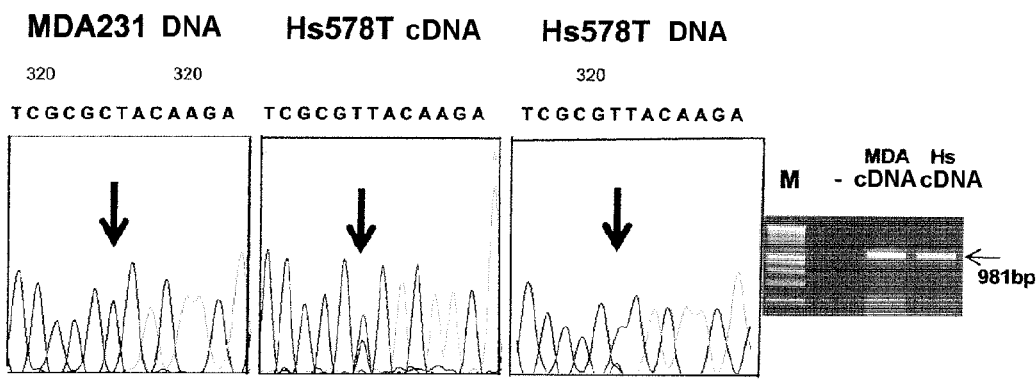
FIG. 6(A-D) is a view showing the identification of the nucleotide at the rs3746083 polymorphic site (in particular, detection of a T nucleotide at the rs3746083 polymorphic site) in Hs578T cells.
Figure 6B:
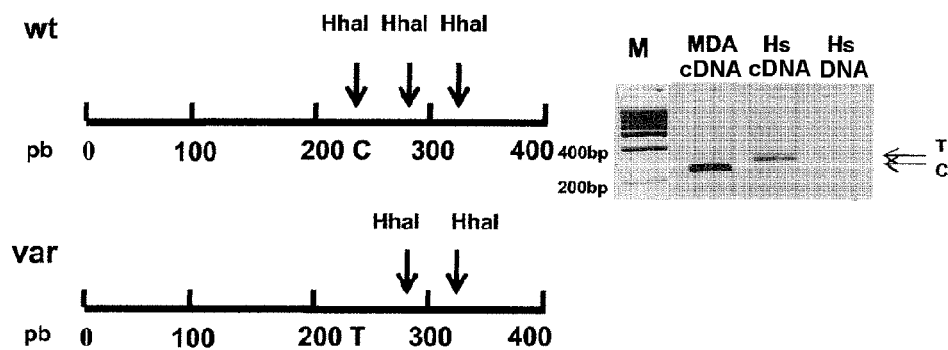
Figure 6:
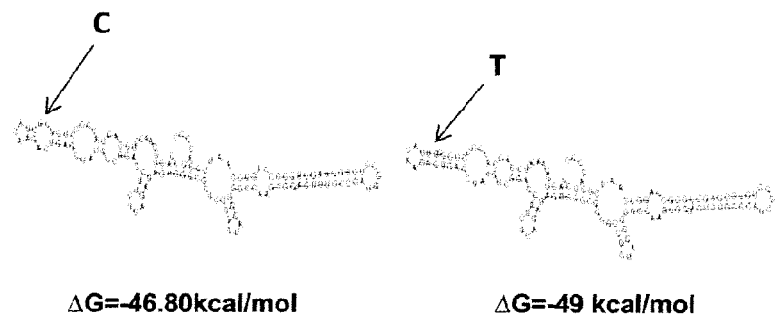

FIG. 6 (A-D) represents identification of the nucleotide at the rs3746083 polymorphic site (in particular, detection of a T nucleotide at the rs3746083 polymorphic site) in Hs578T cells. (A) (SEQ ID NOS: 8-10) Sequence chromatograms and PCR analysis of the TTP coding region of genomic DNA and cDNA obtained from MDA231 and Hs578T cells. (B) Diagram and analysis of digestion of PCR fragments cleaved with the enzyme HhaI. (C) Secondary mRNA structure predicted by the MFOLD software for the wild-type (presence of a C nucleotide at the rs3746083 polymorphic site) and the sequence variant (presence of a T nucleotide at the rs3746083 polymorphic site). (D) TTP mRNA half-life determined by DRB (5,6-dichloro-1-D-ribofuranosylbenzimidazole) kinetics of MCF7, Hs578t and MDA231 cells.

FIG. 7 (A-B) represents the effect of the wild-type TTP (wt) (presence of a C nucleotide at the rs3746083 polymorphic site) or the variant TTP (var) (presence of a T nucleotide at the rs3746083 polymorphic site) on translation. (A) In vitro translation of wild-type (wt) and variant (var) TTP-Myc expression plasmids. (B) Increasing quantities of Trex plasmids (50 ng, 100 ng, 200 ng) carrying the wild-type and variant TTP sequences which were transfected in HEK293 cells. The protein lysates were analyzed by immunoblot. Two independent DNA preparations were used at concentrations of 200 ng. The comparison between samples was carried out after calculating transfection efficiency (as explained in the Materials and Methods section).

FIG. 8 (A-C) represents the functional effect of the variant TTP allele (T allele, presence of a T nucleotide at the rs3746083 polymorphic site) on the stability of target genes. (A) Assay of the activity of the luciferase reporter gene coupled with the 3'UTR of VEGF mRNA after transfection of an empty vector, an expression vector containing the wild-type TTP gene or the variant TTP gene (presence of a T nucleotide at the rs3746083 polymorphic site). Average relative luciferase activities were calculated on the basis of four independent transfections. (B) DRB kinetics and measurement of half-life of endogenous VEGF mRNA after transfection with wild-type or variant TTP constructs. (C) Effect of wild-type TTP and variant TTP on endogenous cyclin D1 mRNA after three hours of DRB treatment. The quantity of mRNA at time 0 is regarded as the reference value (100%).

EXAMPLES

I. Materials and Methods
I.1 Construction of Plasmids

For the TET-Off approach (TET: tetracycline) in MDA231 cells, the pREV-TTP construct was obtained by inserting a 1 kb DNA fragment corresponding to the coding for region of the TTP cDNA (Essafi-Benkhadir et al., 2007) in the HindIII restriction sites of the pREV plasmid (Clontech). The pcDNA4/TO/myc-HysA (Trex-TTP) constructs containing the wild-type sequence (presence of a C nucleotide at the rs3746083 polymorphic site) and the sequence variant of human TTP (presence of a T nucleotide at the rs3746083 polymorphic site) were generated by amplifying a 1 kb region directly from cDNA of Hs578T cells with sense primer (5'CCACTCTCGGCCGACACCCC-3') (SEQ ID NO: 4) and anti-sense primer (5'-GTCACTCAGAAACAGAGATGCG-3') SEQ ID NO: 5) and by inserting the fragment into the pCR2.1-TOPO vector (Invitrogen). The TTP cDNA fragments were then inserted into the pcDNA4/TO/myc-HysA vector (Invitrogen) at the EcoRI restriction site. Two independent plasmid preparations were obtained for each construct.

I.2 RNA Preparation and Analysis by Quantitative PCR

Total RNA was extracted with TRIzol reagent (Invitrogen). Two micrograms of total RNA was used for reverse transcription, using the Superscript First-Strand Synthesis System kit (QIAGEN, Hilden, Germany), with Oligo(dT) primers to prime the synthesis of the first DNA strand. For the real-time PCR, the TaqMan Gene Expression Assay kit (Applied Biosystems) and the qPCR Core kit (Eurogentec) were used. To calculate the relative expression of TTP, VEGF and IL8 mRNA in the cell lines, the 2[ddC(T)] method was used (Schmittgen, 2008) and the RPLP0 gene (Essafi-Benkhadir et al., 2007) was used for normalization. To calculate mRNA stability, 25 µg/ml of 5,6-dichloro-1--D-ribofuranosylbenzimidazole (DRB) was added to cultured breast cancer cells from which RNA was then extracted at various times. The relative quantity of each mRNA at time 0 before the addition of DRB to the culture medium was set at 100%.

I.3 Cell Culture, Transection and Luciferase Test

The breast cancer cell lines MDA231, Hs578T, MCF7, T47D and MCF10 and the human embryonic kidney cell line HEK293 were cultured as previously described (Essafi-Benkhadir et al., 2007, Eckert et al., 2004). RAW264.7 cells were grown in Dulbecco's Modified Eagle's Medium, supplemented with fetal calf serum in a humidified atmosphere of 5% $CO_2$ at 37° C. They were stimulated with lipopolysaccharide (LPS) (Sigma Aldrich) at a concentration of 10 ng/ml. The TTP antibody was validated by immunoblot analysis on protein extracts of LPS-stimulated RAW264.7 cells and HEK293 cells transfected with human form TTP (Lay et al., 1999). Stable clones were obtained by transfecting the pREV-TTP plasmid with Lipofectamine™ 2000 (Invitrogen) and hygromycin-resistant clones were screened by immunoblot after removal of tetracycline from the culture medium. Inactivation of TTP in the MCF7 cells was obtained by transfecting the cells with Lipofectamine and MISSION™ shRNA lentiviral plasmids (SIGMA). Selection of resistant clones was carried out by adding puromycin to the culture medium and screening of selected clones was carried out by qPCR.

The functional test of the TTP rs3746083 polymorphism on translation was carried out on HEK293 cells transfected with plasmids corresponding to the wild-type TTP (wt) (presence of a C nucleotide at the rs3746083 polymorphic site) and the variant TTP (var) (presence of a T nucleotide at the rs3746083 polymorphic site) using the calcium phosphate transfection method (Essafi-Benkhadir et al., 2007). The test was carried out in duplicate with various quantities of pcDNA4/TO/myc-HysA carrying the wild-type TTP sequence and the sequence variant (two independent preparations for each construct). At the same time, 300 ng of plasmid expressing the luciferase reporter gene (plasmid pGL3) were co-transfected as independent controls of the transfection efficiency in each well. The test was carried out as previously described (Essafi-Benkhadir et al., 2007). Transfection efficiency was calculated from luciferase level normalized to protein quantity. Only cells that showed the same level of transfection efficiency (difference <20%) were analyzed. Laemmli lysis solution was added to the cells. The proteins of the extracts were separated by SDS-PAGE then transferred on a polyvinylidene difluoride membrane (Immobilon-P; Millipore, Billerica, Mass.). Immunoreactive proteins are revealed with the Enhanced Chemiluminescence detection system (ECL; Pierce Chemical, Rockford, Ill.).

I.4 Treatment with Calf Intestinal Alkaline Phosphatase (CIAP)

For experiments with CIAP (New England Biolabs, Ipswich, Mass.), MDA231 cells were deprived of tetracycline for 24 hours before analysis. The cells were then lysed in lysis buffer (1% Triton X-100, 50 mM Tris, pH 8.5, 100 mM NaCl and 0.5 mM EDTA). CIAP (35 U) was added to the lysates for 1 hour at 37° C. The reaction was stopped by adding Laemmli lysis buffer.

I.5 Measurement of VEGF and IL-8 Secretion

The presence of VEGF and IL-8 in the cell supernatants was measured using the enzyme-linked immunosorbent assay (ELISA) kit for human VEGF and IL-8 (Pierce Biotechnology, Rockford, Ill.).

I.6 Patients and Association Studies 92 women with breast cancer and 89 women as controls were analyzed for the presence of a T nucleotide at the rs3746083 polymorphic site. All the patients suffering from cancer had very aggressive tumors with amplification of the HER2 gene (HER2-positive). They were all treated with Herceptin® (trastuzumab), a monoclonal antibody directed against HER2. Genomic DNA was extracted from peripheral blood leukocytes using standard techniques. For the SNP NM_003407.2: 367C>T (presence of a T nucleotide at the rs3746083 polymorphic site), a single 400 bp amplicon was generated using the primers 103F (5'-GACCATG-GAGGGACTGAG-3') SEQ ID NO: 6) and 103R (5'-GC-CCTGGAGGTAGAACTTGT) SEQ ID NO: 7), and by following the following PCR conditions: 200 ng of genomic DNA, 50 pM of each primer, 200 μM of each dNTP, 1× buffer, 0.9 units of Taq polymerase (AmpliTaq Gold—Applied Biosystems, Foster City, Calif., USA) and 1.5 mM MgCl$_2$, in a PCR reaction volume of 50 μl. Initial denaturation at 95° C. for 10 minutes is followed by 35 amplification cycles at 95° C. for 45 seconds, 62° C. for 45 seconds, 72° C. for 45 seconds, then a final extension at 72° C. for 10 minutes. The presence or absence of the T allele of the variant at the rs3746083 locus (presence of a T nucleotide at the rs3746083 polymorphic site; NM_003407.2: 367C>T ) is evaluated by digestion with the restriction enzyme HhaI (following the instructions of the manufacturer—New England BioLabs). After enzymatic digestion, the samples are deposited on a 3% agarose gel.

I.7 Statistical Analysis

Allele frequencies are estimated from genotype data. The patient group and the control group are compared with the Fisher exact test by defining p=0.05 as the statistical significance criterion. Hardy-Weinberg equilibrium is tested with the chi-squared test in both the control groups and the patient group. For the clinical study, tumor parameters were compared by ANOVA. Survival estimates were calculated using the Kaplan-Meier method. Differences between survival durations were evaluated using the log-rank test. The chi-squared test was used to determine associations between patient genotypes, toxicity (hematologic, digestive) and response to trastuzumab-based therapy.

II. Results

II.1 Expression of TTP, VEGF and IL8 in Breast Cancer Cell Lines

Figure 1B:
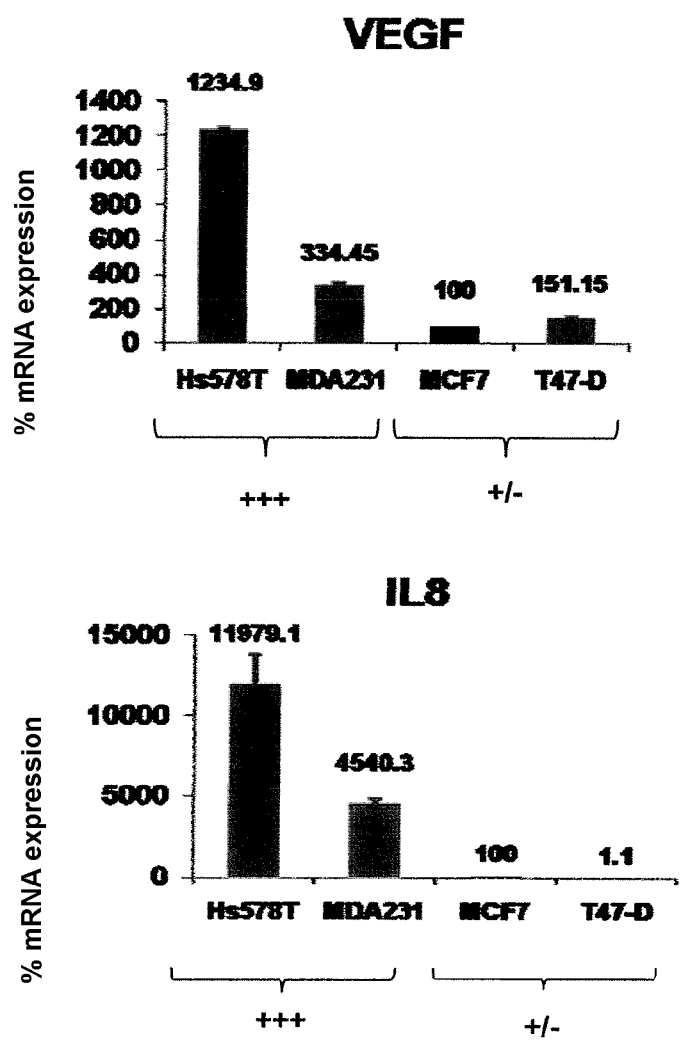
Figure 1C:
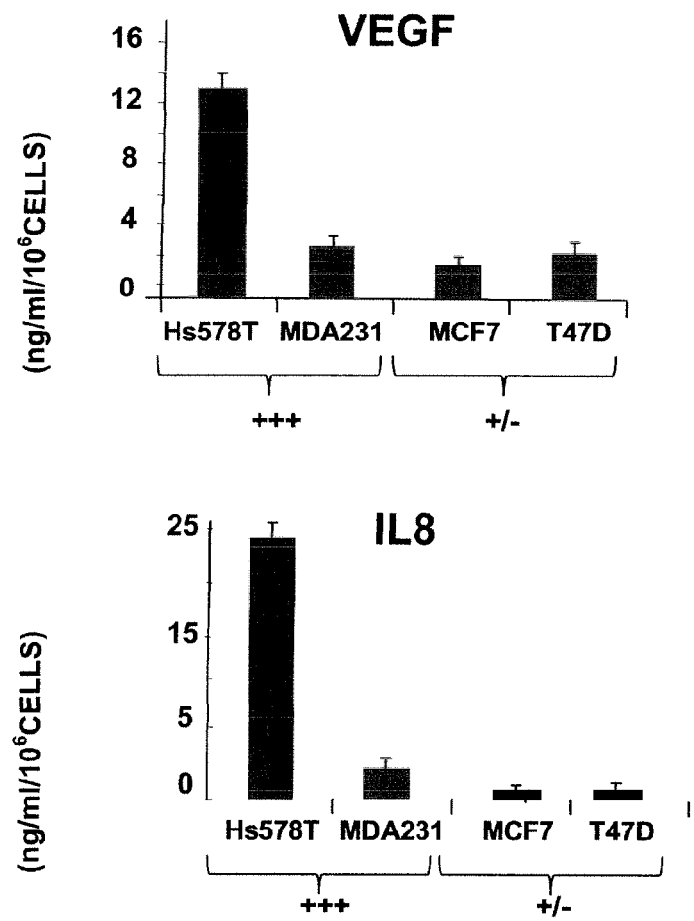

The levels of TTP protein were analyzed by immunoblot in several breast cancer cell lines: MDA231, Hs578T, MCF7 and T47D. MDA231 and Hs578T are very aggressive cell lines, characterized by a mesenchymal phenotype, a lack of expression of estrogen and progesterone receptors and HER2 receptor (also called a "triple-negative" phenotype), whereas MCF7 and T47D have a less aggressive epithelial phenotype and expression of estrogen and progesterone receptors without amplification of the HER2 protein (Eckert et al., 2004). The expected size of the TTP protein is 35 kDa but it frequently migrates in the form of a 45 kDa to 47 kDa band during conventional SDS-PAGE immunoblot analysis using both commercial antibodies (Suswam et al., 2008, Al-Souhibani et al., 2010) and "house" antibodies (Essafi-Benkhadir et al. 2007). It was observed that two cancer cell lines, MDA231 and Hs578T, did not express the protein with the expected size, while MCF7 and T47D cells expressed it at levels comparable to those of MCF10, a non-tumorigenic, immortalized breast cell line (FIG. 1A). It was examined whether the lack of expression of the TTP protein could be correlated with a higher production of angiogenic factors such as VEGF and IL8 in triple-negative cells (MDA231 and Hs578T) than in less aggressive cell lines (MCF7 and T47D). To that end, the levels of mRNA of these factors were determined by quantitative real-time PCR and the levels of secreted proteins determined by ELISA in the four lines. MDA231 and Hs578T cells do not express the TTP protein but produce a high quantity of VEGF and IL8 in terms of both mRNA and proteins (FIGS. 1B and 1C). These data underlie a correlation between TTP levels and breast tumor cell aggressiveness.

Figure 2A:
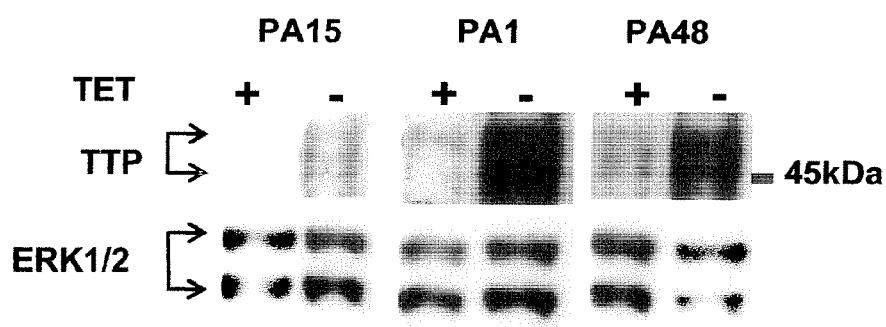
FIG. 2(A-B) is a view showing the TTP-MDA 231 inducible clones.
Figure 2B:
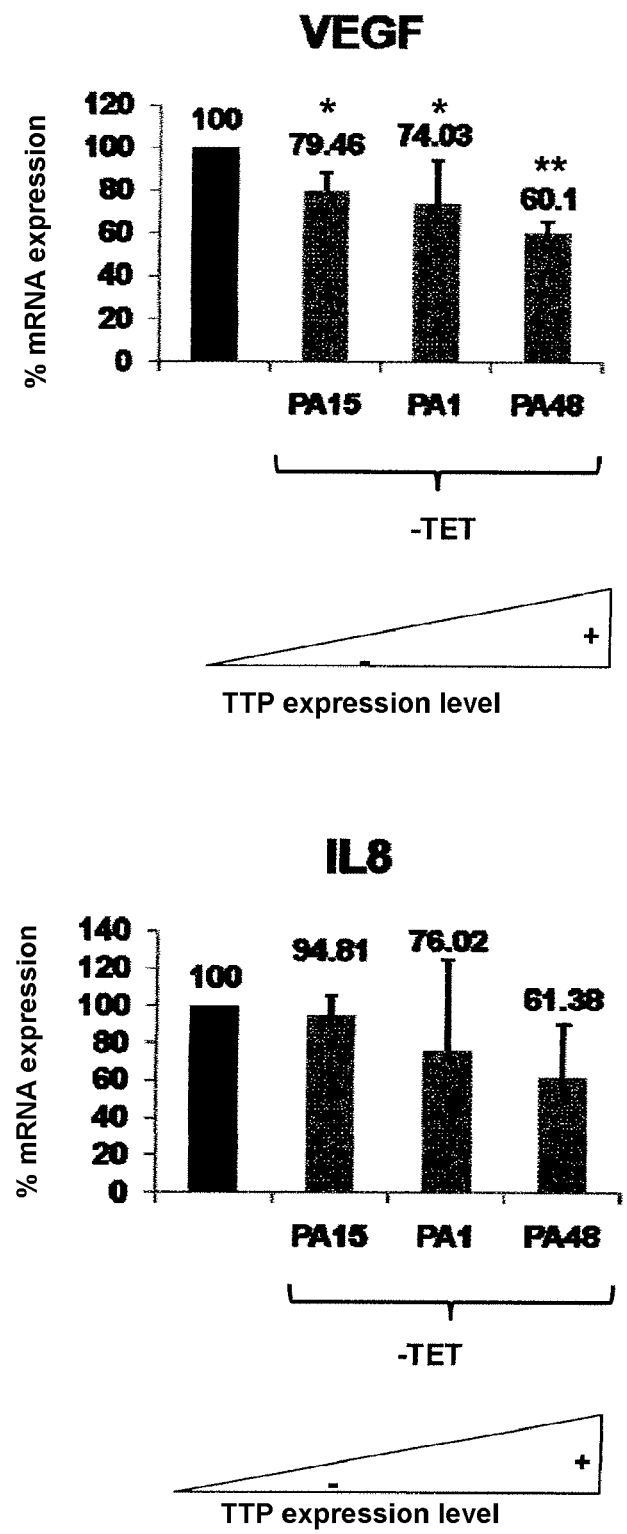

II.2 Modulation of the Expression of TTP Affects the Expression of Angiogenic Factors in Relatively Non-aggressive or Very Aggressive Breast Cancer Cell Lines To study the correlation between the TTP protein and angiogenic factors in breast cancer, clones of MDA231/TET-OFF cells stably transfected with the Myc-epitope tagged, tetracycline-inducible TTP gene were generated. As previously observed for HeLa/TTP cells, the TET-OFF model is more appropriate for the study of genes involved in cell proliferation and avoids the selection of false-positive clones (Suswam et al., 2008). In the presence of tetracycline, the TTP protein is not expressed. Removing tetracycline from the medium enables TTP induction. One clone (PA15) with weakly inducible expression and two clones (PA1 and PA48) with highly inducible expression of TTP protein were obtained (FIG. 2A). To show the effect of TTP protein on the production of VEGF and IL8 mRNA, quantitative real-time RT-PCR was carried out and a dose-dependent effect of TTP protein on the expression of VEGF and IL8 mRNA was observed (FIG. 2B). This experiment confirms that reduction in levels of angiogenic factor mRNA depends on the level of TTP protein.

To evaluate the correlation between the expression of TTP protein and the production of angiogenic factors, the data obtained for MDA231 cells were confirmed by means of a complementary approach: inactivation (silencing) of TTP protein expression in the MCF7 breast cancer cell line, which expresses the protein normally. As previously observed, MCF7 cells have an epithelial morphology and are characterized by distinctly detectable levels of TTP protein.

Figure 3A:
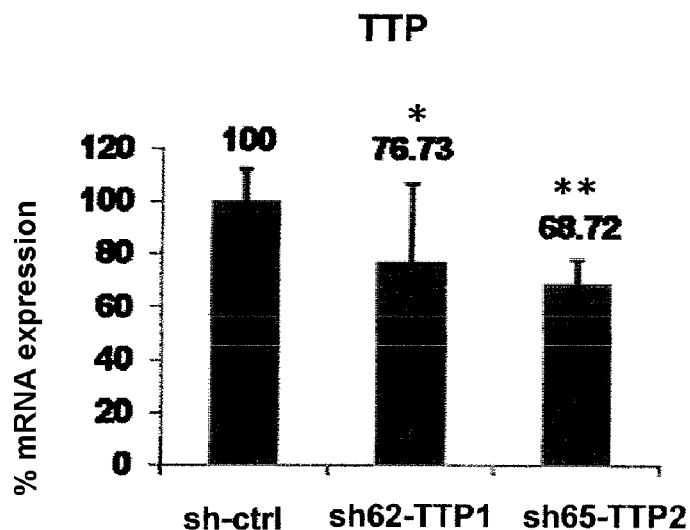
FIG. 3(A-C) is a view showing the stable MCF7 clones obtained by transfection of shCTRL, sh62-TTP1 and sh65-TTP2 sequences.
Figure 3B:
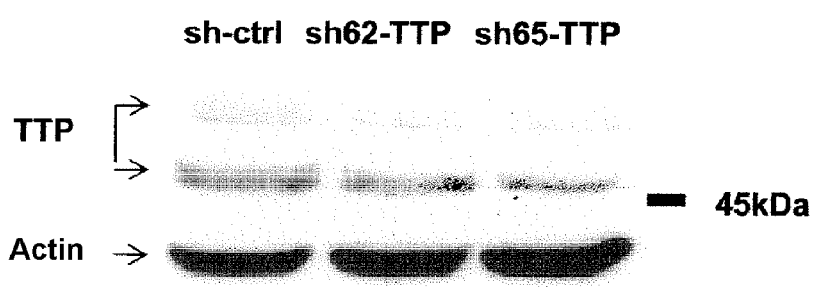
Figure 3C:
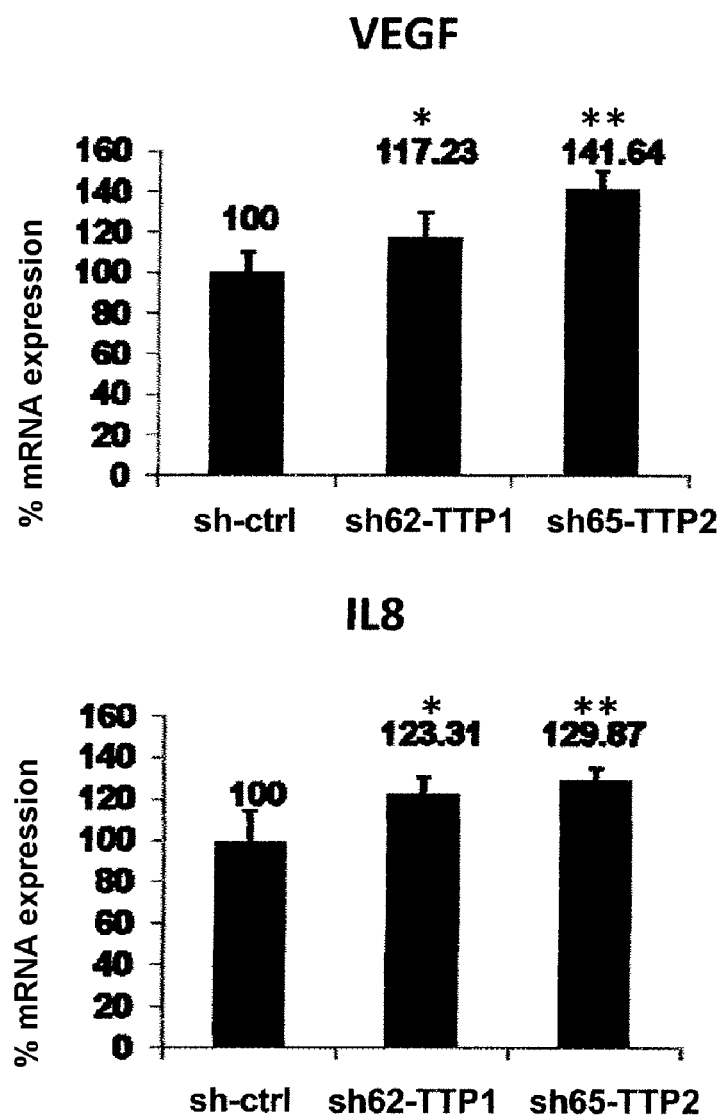

Two clones expressing two independent sh-RNA (sh62.TTP and sh65.TTP) have a reduction of 30% and 40%, respectively, of TTP mRNA levels, in relation to the control (sh-ctrl) (FIG. 3A). Immunoblot analysis confirms a clear reduction in TTP levels (FIG. 3B). Simultaneously to the reduction in TTP protein, an increase in VEGF and IL8 mRNA levels was observed in the sh62.TTP and sh65.TTP cells, which confirms an inverse correlation between TTP level and VEGF and IL8 levels (FIG. 3C).

II.3 the Effect of TTP on the Proliferation of Breast Cancer Cells

Figure 4A:
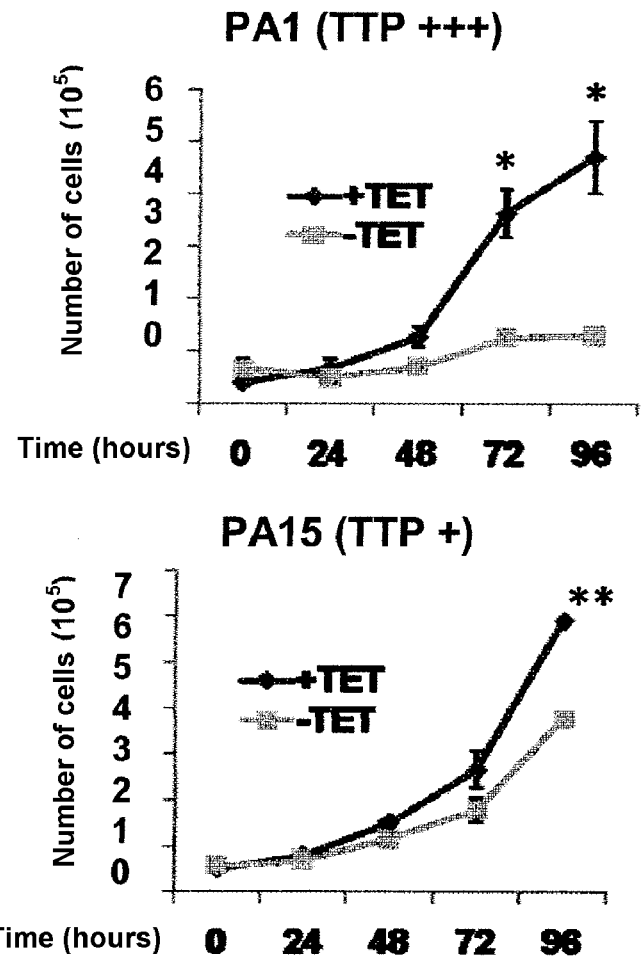
FIG. 4(A-C) is a view showing the effect of TTP expression on the proliferation of inducible MDA231-TTP clones and stable shTTP-MCF7 clones.
Figure 4B:
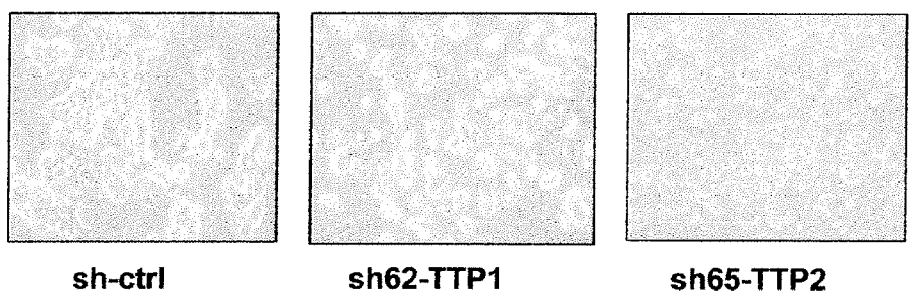
Figure 4C:
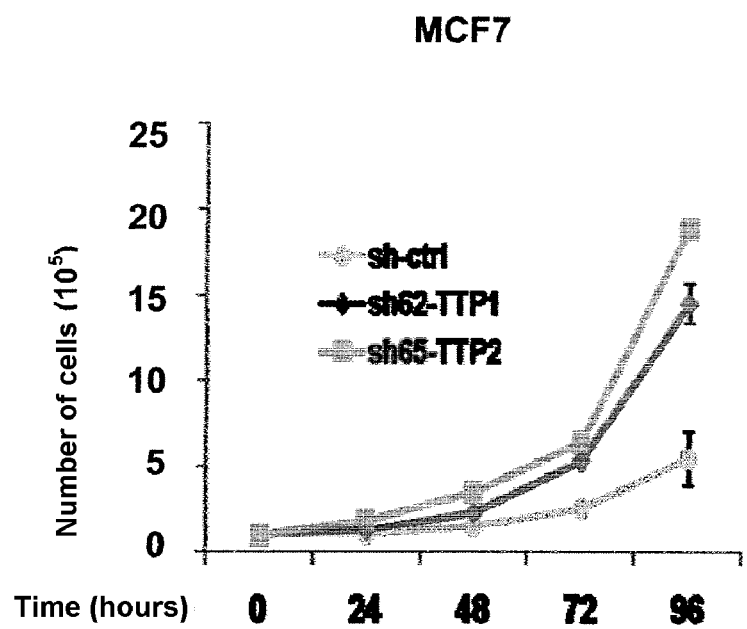

Another tumorigenic phenotype which can be modulated by the expression of TTP protein is the proliferation rate of cancer cells (Brennan et al., 2009). In the two MDA231 clones (PA1 and PA15), which express the TTP protein at high and low levels, respectively, a reduction in the proliferation rate depends on the expression of TTP protein (FIG. 4A). During the proliferation of MDA231 clones (up to four days), no morphological change and no increase in cell death or apoptosis were noted, as observed for glioma or HeLa cells (Suswam et al., 2008, Brennan et al., 2009). Furthermore, stable MCF7-TTP knockdown clones (sh62-TTP1 and sh65-TTP2) were used to confirm the effect of TTP protein expression on proliferation. From a morphological point of view, these clones have the ability to grow in colony form, an effect which could corroborate the involvement of loss of TTP protein in the epithelial-mesenchymal transition (Gebeshuber et al., 2009) (FIG. 4B). The two clones (sh62-TTP1 and sh65-TTP2) exhibited a significant increase in proliferation rate correlated with the dose-dependent disappearance of TTP protein (FIG. 4C). As previously described for the expression of VEGF and IL8 mRNA, a dose-dependent effect on proliferation was observed.

II.4 TTP Expression in Breast Cancer

Figure 5A:
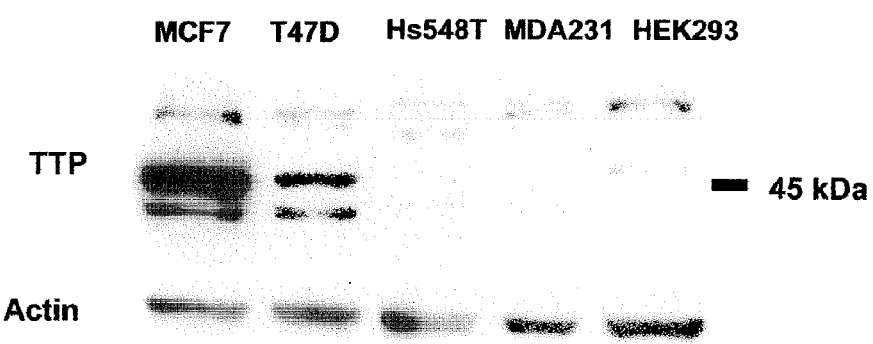
FIG. 5(A-B) is a view showing the comparative expression of TTP in breast cancer cell lines.
Figure 5B:
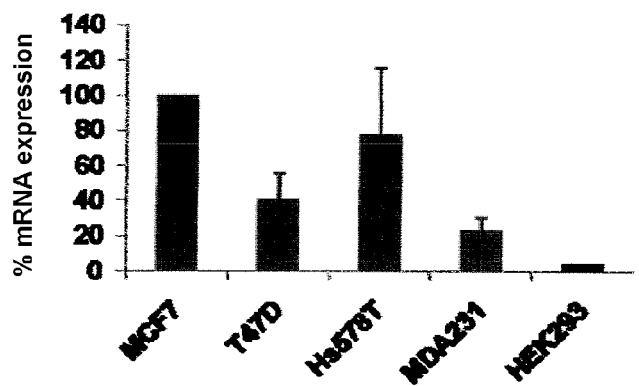

Considered as a whole, the present data clearly point to a crucial role of TTP protein levels in the production of two angiogenic factors, VEGF and IL8, and the regulation of breast cancer cell proliferation. These results clearly corroborate the published data which show the frequent suppression of TTP protein expression in breast cancers. Consequently, TTP protein was proposed as a prognostic factor for tumor aggressiveness (Brennan et al., 2009). As the possibility of using TTP protein expression rate as a prognostic factor for breast cancer is very promising, the relative quantity of TTP mRNA and the TTP protein levels in the breast cancer cell lines described above were tested in order to show a correlation between levels of mRNA and TTP protein. MCF7, MDA231, T47D and Hs578T cells were tested and human embryonic kidney cells (HEK293) were used as a negative control given that these cells have been described as negative for the expression of TTP protein (Lay et al., 1999). As shown in FIG. 5A, TTP protein can be clearly detected in MCF7 and T47D cells whereas it is absent or weakly expressed in HEK293, MDA231 and Hs578T cells. TTP mRNA was analyzed using the $\Delta\Delta CT$ method. The mRNA level in MCF7 cells was regarded as the reference value (100%). The lowest TTP mRNA levels were found in MDA231 cells, while significant TTP mRNA levels were detected in MCF7 and T47D cells. Surprisingly, Hs578T cells, which do not express the protein, have clearly detectable levels of TTP mRNA (FIG. 5B). These data show an evident lack of correlation between the expression levels of mRNA and of TTP protein. This lack of correlation can be due either to a shorter half-life of TTP mRNA or to a difference of translation levels of its mRNA.

II.5 Genetic Analysis of the TTP Gene

To study the lack of correlation between levels of TTP protein and mRNA in Hs578T cells, the region coding for the TTP protein on genomic DNA was sequenced and the genomic DNA of MCF7 cells was used as a control. A single-nucleotide polymorphism (SNP) was detected in Hs578T cells (rs3746083=NM_003407.2: 367C>T, the presence of a T nucleotide at the rs3746083 polymorphic site) which modifies the codon corresponding to arginine, transforming CGC into CGT (R103R). A case-control study was carried out to evaluate the role played by the 367C>1 variant (presence of a T nucleotide at the rs3746083 polymorphic site) in breast carcinogenesis by studying a group of women suffering from breast cancer (92 individuals: patient group) and a group of women as controls (89 individuals: control group). All the patients had very aggressive tumors with amplification of the HER2 gene (HER2-positive) and all the cases were treated with Herceptin® (trastuzumab), a monoclonal antibody directed against HER2 (Hall et al., 2009). 13 C/T heterozygotes at the rs3746083 polymorphic site were identified in the patient group (frequency of the T allele=14.1%) and 5 C/T heterozygotes at the rs3746083 polymorphic site were identified in the control group (frequency of the T allele=5.6%). The allele frequencies of the C and T alleles of the rs3746083 polymorphism in Table 1 revealed an increase in the frequency of the T allele in the patient group, however not reaching the threshold of statistical significance (Chi$^2$ test p=0.095 confirmed using the Fisher test p=0.080, OR=2.7, CI95% [0.9-10.3]). Furthermore, it was examined whether the 367C>T variant (presence of a T nucleotide at the rs3746083 polymorphic site) could be associated with other clinical parameters such as survival rate. No correlation with survival rate was identified. However, a different distribution of the T allele of the rs3746083 polymorphism was observed with regard to the response of patients to treatment with Herceptin® (trastuzumab). As indicated in Table 2, the T allele of the rs3746083 polymorphism was distinctly more frequent in the group of patients resistant to Herceptin® (trastuzumab) than in the control group, with a statistically significant value (Chi$^2$ test p=0.010 confirmed using the Fisher test p=0.0093, OR=8.0, CI95% [1.9-33.4]). These data indicate that the presence of a T nucleotide at the rs3746083 polymorphic site for at least one allele of the gene coding for the TTP protein has a functional effect on TTP protein expression and is related to a differential reaction of patients to trastuzumab (Herceptin®) treatment.

TABLE 1

Distribution of the C > T variant (presence of a T nucleotide at the rs3746083 polymorphic site) in 89 control women and 92 patients suffering from HER2-positive breast cancer.

| Group | C/T heterozygosity at the rs3746083 polymorphic site | C/C homozygosity at the rs3746083 polymorphic site | Total |
| --- | --- | --- | --- |
| Controls | 5 (5.6%) | 84 (94.4%) | 89 (100%) |
| Patients | 13 (14.1%) | 79 (85.9%) | 92 (100%) |

TABLE 2

Distribution of the C > T variant (presence of a T nucleotide at the rs3746083 polymorphic site) in 54 patients suffering from breast cancer and treated with Herceptin® (trastuzumab).

| Patients | Non-responsive | | Total |
| --- | --- | --- | --- |
| | 6 (40%) C/T heterozygosity at the rs3746083 polymorphic site | 9 (60%) C/C homozygosity at the rs3746083 polymorphic site | 15 (100%) |
| Responsive | 3 (7.7%) | 36 (92.3%) | 39 (100%) |

II.6 Functional Analysis of the 367C>T Genetic Variant (NM_003407.2) (Presence of a T Nucleotide at the rs3746083 Polymorphic Site)

Figure 6D:
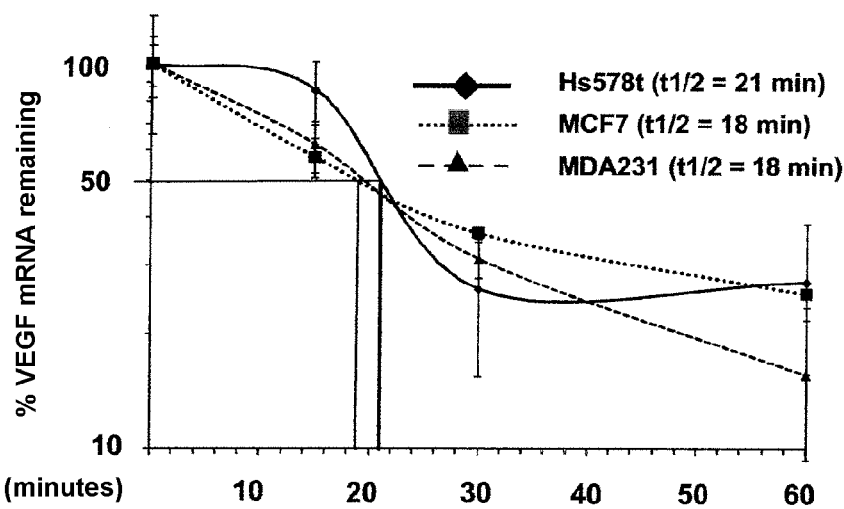
Figure 7A:
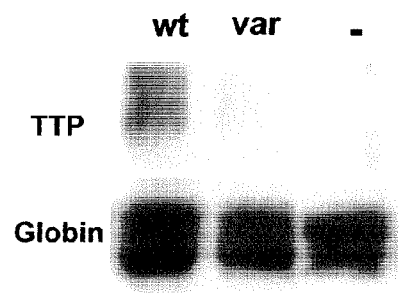
FIG. 7(A-B) is a view showing the effect of the wild-type TTP (wt) (presence of a C nucleotide at the rs3746083 polymorphic site) or the variant TTP (var) (presence of a T nucleotide at the rs3746083 polymorphic site) on translation.
Figure 7B:
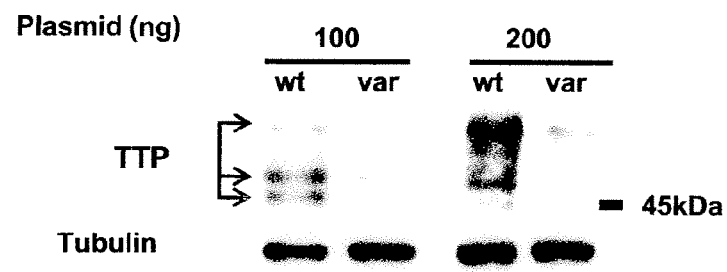

Considering the results obtained during the genetic analysis, it was examined whether the 367C>T variant (NM_003407.2) (presence of a T nucleotide at the rs3746083 polymorphic site) could be responsible for the divergence between the levels of mRNA and TTP protein observed in Hs578T cells. First, it was examined whether the 367C>T change (NM_003407.2) could affect expression of the gene by interfering with mRNA stability or protein translation (Sauna, 2007). PCR analysis of TTP cDNA obtained from Hs578T cells did not reveal the existence of abnormal alternative transcripts in these cells in comparison with MDA231 cells (FIG. 6A). In order to verify that both the wild-type (C allele) (wt) and the variant allele (T allele) (var) were transcribed, the identification of the nucleotide at the rs3746083 polymorphic site was carried out on the one hand by analyzing digestion with the enzyme HhaI and on the other hand by sequencing PCR products resulting from genomic DNA and cDNA obtained from Hs578T cells. The two techniques showed that the T allele (of the rs3746083 polymorphism) was expressed more than the wild-type C allele (of the rs3746083 polymorphism) in Hs578T cells (FIGS. 6A and 6B). Furthermore, prediction analysis of the TTP mRNA structure using the MFold program (http://rna.tbi.univie.ac.at/cgi-bin/RNAfold.cgi) showed a more stable secondary structure of mRNA molecules corresponding to the T allele (of the rs3746083 polymorphism) in relation to that of mRNA molecules corresponding to the C allele (of the rs3746083 polymorphism) (FIG. 6C). The half-life of TTP mRNA is 18 minutes in MCF7 and MDA231 cells and 21 minutes in Hs578T cells (FIG. 6D). As highly stable RNA structures can affect the translation level of the corresponding mRNA, it was assumed that highly stable and abundant mRNA molecules could be associated with lower protein levels (Nackley et al., 2006). To test this hypothesis functionally, in vitro transcription/translation experiments were carried out using a TTP construct tagged both for the wild-type allele (C allele of the rs3746083 polymorphism) and for the variant allele (T allele of the rs3746083 polymorphism). Thus, the translation levels of the wild-type TTP gene (wt) (presence of a C nucleotide at the rs3746083 polymorphic site) are higher than those of the variant TTP gene (var) (presence of a T nucleotide at the rs3746083 polymorphic site) (FIG. 7A). To confirm these data, an experimental model was developed by cloning both full-length coding regions (the wild-type C allele and the variant T allele of the rs3746083 polymorphism) in the eukaryotic expression vector pcDNA4/TO/myc-His in order to proceed to transient transfection in the TTP-negative HEK293 cell line. A luciferase reporter gene was co-transfected as a control of transfection efficiency. Experiments with various quantities of TTP plasmids (100, 200 and 500 ng of DNA/$10^5$ cells) were carried out to determine the optimal TTP concentration that did not affect luciferase transcription and/or stability or did not induce massive cell death. No effect was observed on cell death but the transfection of 500 ng, both for the wild-type construct (C allele of the rs3746083 polymorphism) and for the TTP variant (T allele of the rs3746083 polymorphism), was excluded because it significantly affected luciferase activity. By comparing only the samples characterized by comparable transfection efficiency, we show that the wild-type TTP plasmid (C allele of the rs3746083 polymorphism) produced a greater quantity of protein than the variant TTP plasmid (T allele of the rs3746083 polymorphism) when 100 or 200 ng of expression plasmids are transfected (FIG. 7B).

Figure 8A:
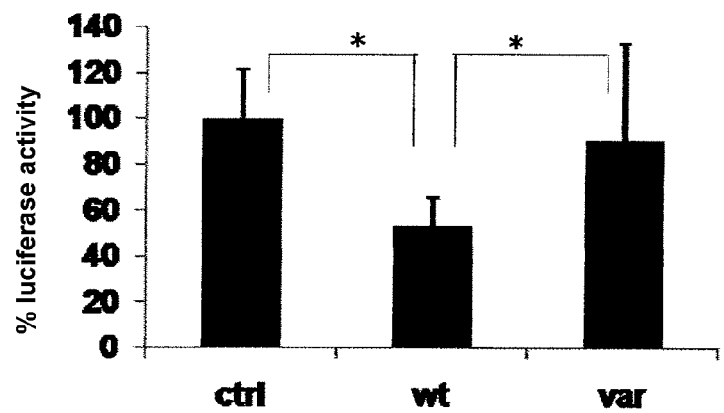
FIG. 8(A-C) is a view showing the functional effect of the variant TTP allele (T allele, presence of a T nucleotide at the rs3746083 polymorphic site) on the stability of target genes.
Figure 8B:
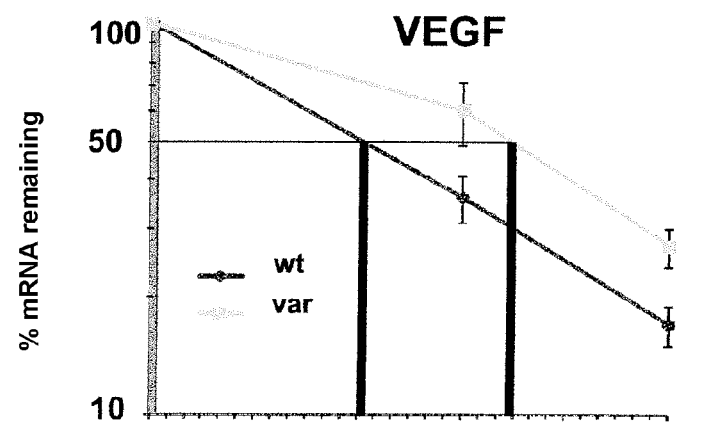
Figure 8C:
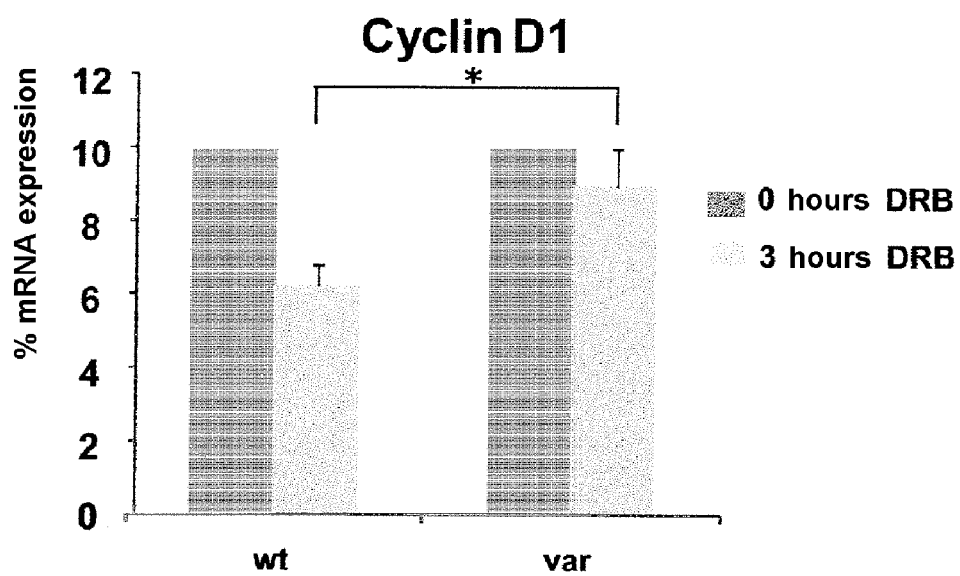

To further study the differences between the wild-type (C allele of the rs3746083 polymorphism) and variant (T allele of the rs3746083 polymorphism) TTP constructs, a functional assay was carried out testing the effect of both plasmids on the VEGF 3'UTR, a well-known target of TTP protein, cloned downstream from the luciferase reporter gene (Essafi-Benkhadir et al., 2007). We note that when HEK293 cells were transfected with the wild-type TTP gene, a decrease in luciferase activity was observed in relation to the control (pcDNA4/TO/myc-His empty vector), but transfection of the variant form of TTP gives luciferase activity equivalent to that obtained after transfection of the empty vector (FIG. 8A). To validate these results, the half-life of endogenous VEGF mRNA was verified in HEK293 cells. A significant difference was obtained 24 hours after transfection of wild-type TTP plasmids. Transfection of the variant form of TTP does not significantly affect the half-life of VEGF mRNA (FIG. 8B). To confirm these data, transcription was inhibited using DRB and the expression of cyclin D1 was verified, cyclin D1 mRNA being another endogenous target of TTP protein (Marderosian et al., 2006). As shown in FIG. 8C, after 3 hours of DRB treatment, the quantity of cyclin D1 mRNA decreased only after transfection of the wild-type TTP gene, the variant form of TTP having no effect. The whole of these data show that the forms of TTP mRNA corresponding to the T allele of the rs3746083 polymorphism (presence of a T nucleotide at the rs3746083 polymorphic site) were not translated with the same efficiency in vitro and in vivo, resulting in lower protein levels. The presence of TTP mRNA corresponding to the T allele of the rs3746083 polymorphism (presence of a T nucleotide at the rs3746083 polymorphic site) is expressed by lower protein levels resulting in an increase in the half-life of target mRNA.

BIBLIOGRAPHICAL REFERENCES

Al-Souhibani, N., Al-Ahmadi, W., Hesketh, J. E., Blackshear, P. J., Khabar, K. S. (2010) The RNA-binding zinc-finger protein tristetraprolin regulates AU-rich mRNAs involved in breast cancer-related processes. *Oncogene.*, 29, 4205-4215.

Bargmann C I, Hung M C, Weinberg R A. 1986. The neu oncogene encodes an epidermal growth factor receptor-related protein. Nature January 16-22; 319(6050):226-30

Brennan, S. E., Kuwano, Y., Alkharouf, N., Blackshear, P. J., Gorospe, M., Wilson, G. M. (2009) The mRNA-destabilizing protein tristetraprolin is suppressed in many cancers, altering tumorigenic phenotypes and patient prognosis. *Cancer Res.*, 69, 5168-5176.

Chen J S, Lan K, Hung M C. 2003 Strategies to target HER2/neu overexpression for cancer therapy. Drug Resist Updat. June; 6(3):129-36. Review. Erratum in: Drug Resist Updat. 2003 October; 6(5):296.

De Laurentiis, M., Cancello, G., Zinno, L., Montagna, E., Malorni, L., Esposito, A., Pennacchio, R., Silvestro, L., Giuliano, M., Giordano, A., et al. (2005). Targeting HER2 as a therapeutic strategy for breast cancer: a paradigmatic shift of drug development in oncology. Ann Oncol 16 *Suppl* 4, iv7-iv13.

Eckert, L. B., Repasky, G. A., Ulkü, A. S., McFall, A., Zhou, H., Sartor, C. I., Der, C. J. (2004) Involvement of Ras activation in human breast cancer cell signaling, invasion, and anoikis. *Cancer Res.*, 64, 4585-4592.

Essafi-Benkhadir, K., Onesto, C., Stebe, E., Moroni, C., Pages, G. (2007) Tristetraprolin inhibits Ras-dependent Tumor vascularization by inducing Vascular Endothelial Growth factor mRNA degradation. *Mol. Biol. Cell.*, 18, 4648-4658.

Gebeshuber, C. A., Zatloukal, K., Martinez, J. (2009) miR-29a suppresses tristetraprolin, which is a regulator of epithelial polarity and metastasis. *EMBO Rep.*, 10, 400-405.

Gianni L, Dafni U, Gelber R D, Azambuja E, Muehlbauer S, Goldhirsch A, Untch M, Smith I, Baselga J, Jackisch C, Cameron D, Mano M, Pedrini J L, Veronesi A, Mendiola C, Pluzanska A, Semiglazov V, Vrdoljak E, Eckart M J, Shen Z, Skiadopoulos G, Procter M, Pritchard K I, Piccart-Gebhart M J, Bell R; Herceptin Adjuvant (HERA) Trial Study Team. 2011 Treatment with trastuzumab for 1 year after adjuvant chemotherapy in patients with HER2-positive early breast cancer: a 4-year follow-up of a randomised controlled trial. Lancet Oncol. March; 12(3): 236-44. Epub 2011 Feb. 25.

Hall, P. S., Cameron, D. A. (2009) Current perspective—trastuzumab. *Eur. J. Cancer*, 45, 12-18.

Johnson, B. A., Geha, M., Blackwell, T. K. (2000) Similar but distinct effects of the tristetraprolin/TIS11 immediate-early proteins on cell survival. *Oncogene,* 19, 1657-1664.

Lai, W. S., Carballo, E., Strum, J. R., Kennington, E. A., Phillips, R. S., Blackshear, P. J. (1999) Evidence that tristetraprolin binds to AU-rich elements and promotes the deadenylation and destabilization of tumor necrosis factor alpha mRNA. *Mol. Cell. Biol.,* 19, 4311-4323.

Marderosian, M., Sharma, A., Funk, A. P., Vartanian, R., Masri, J., Jo, O. D., Gera, J. F. (2006) Tristetraprolin regulates Cyclin D1 and c-Myc mRNA stability in response to rapamycin in an Akt-dependent manner via p38 MAPK signaling. *Oncogene,* 25, 6277-6290.

Nackley, A. G., Shabalina, S. A., Tchivileva, I. E., Satterfield, K., Korchynskyi, O., Makarov, S. S., Maixner, W., Diatchenko, L. (2006) Human catechol-O-methyltransferase haplotypes modulate protein expression by altering mRNA secondary structure. *Science,* 314, 1930-1933.

Nahta R, Esteva F J. 2006 HER2 therapy: molecular mechanisms of trastuzumab resistance. Breast Cancer Res.; 8(6):215.

Sauna, Z. E., Kimchi-Sarfaty, C., Ambudkar, S. V., Gottesman, M. M. (2007) Silent polymorphisms speak: how they affect pharmacogenomics and the treatment of cancer. *Cancer Res.,* 67, 9609-9612.

Scatchard, G. 1949. The attractions of proteins for small molecules and ions. Ann. N.Y. Acad. Sci. 51 660-672

Schmittgen, T. D., Livak, K. J. (2008) Analyzing real-time PCR data by the comparative C(T) method. *Nat. Protoc.,* 3, 1101-1108.

Slamon, D. J., Clark, G. M., Wong, S. G., Levin, W. J., Ullrich, A., and McGuire, W. L. (1987). Human breast cancer: correlation of relapse and survival with amplification of the HER-2/neu oncogene. Science 235, 177-182.

Suswam, E., Li, Y., Zhang, X., Gillespie, G. Y, Li, X., Shacka, J. J., Lu, L., Zheng, L., King, P. H. (2008) Tristetraprolin down-regulates interleukin-8 and vascular endothelial growth factor in malignant glioma cells. *Cancer Res.,* 68, 674-682.

Yamamoto T, Ikawa S, Akiyama T, Semba K, Nomura N, Miyajima N, Saito T, Toyoshima K. 1986 Similarity of protein encoded by the human c-erb-B-2 gene to epidermal growth factor receptor. Nature. January 16-22; 319 (6050):230-4.

The invention claimed is:

1. An in vitro or ex vivo method for determining the response of a patient to treatment with trastuzumab and treating a patient determined to be responsive to treatment with trastuzumab, said method comprising the steps of:
  i) identifying (a) or (b) at a rs3746083 polymorphic site at position 367 in a nucleotide sequence of SEQ ID NO: 3 coding for a tristetraprolin protein in a biological sample from said patient:
    (a) heterozygosity (T/C) or homozygosity (T/T) indicating that said patient is determined to be not responsive to treatment with trastuzumab;
    (b) homozygosity (C/C) indicating that said patient is determined to be responsive to the treatment with trastuzumab;
  ii) determining the level of the tristetraprolin protein in a biological sample from said patient and comparing it with at least one reference value, wherein the level of the tristetraprolin protein in the biological sample is greater than or equal to a reference value, the patient is predicted to be responsive to the treatment with trastuzumab; and
  iii) administering trastuzumab to said patient being determined to be responsive to treatment with trastuzumab, wherein said patient is suffering from HER2-positive breast cancer.

2. An in vitro or ex vivo method of prognosis or diagnosis of HER2-positive breast cancer in a patient and treating a patient determined to have said cancer, comprising:
  i) identifying (a) or (b) at a rs3746083 polymorphic site at position 367 in a nucleotide sequence of SEQ ID NO: 3 coding for a tristetraprolin protein in a biological sample from said patient;
    (a) heterozygosity (T/C) or homozygosity (T/T) indicating that said patient is determined to be not responsive to treatment with trastuzumab,
    (b) homozygosity (C/C) indicating that said patient is determined to be responsive to the treatment with trastuzumab, and
  ii) administering trastuzumab to said patient being determined to have HER2-positive breast cancer.

3. The method according to claim 2, wherein the cancer is HER2-positive breast cancer with a poor prognosis.

* * * * *